(12) United States Patent
Houser et al.

(10) Patent No.: US 8,142,461 B2
(45) Date of Patent: Mar. 27, 2012

(54) SURGICAL INSTRUMENTS

(75) Inventors: Kevin L. Houser, Springboro, OH (US);
Andrew M. Zwolinski, Cincinnati, OH (US); Tracy D. Lopes, Mason, OH (US); Prasanna Malaviya, Mason, OH (US); Daniel W. Price, Loveland, OH (US); Louis T. DeLuca, Flower Mound, TX (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1034 days.

(21) Appl. No.: 11/726,620

(22) Filed: Mar. 22, 2007

(65) Prior Publication Data
US 2008/0234708 A1    Sep. 25, 2008

(51) Int. Cl.
*A61B 17/32* (2006.01)
(52) U.S. Cl. .................................................. 606/169
(58) Field of Classification Search ............ 604/22; 606/127–128, 159, 167–173, 180
See application file for complete search history.

(56) References Cited

U.S. PATENT DOCUMENTS

| | | |
|---|---|---|
| 2,736,960 A | 3/1956 | Armstrong |
| 2,849,788 A | 9/1958 | Creek |
| 3,015,961 A | 1/1962 | Roney |
| 3,526,219 A | 9/1970 | Balamuth |
| 3,614,484 A | 10/1971 | Shoh |
| 3,636,943 A | 1/1972 | Balamuth |
| 3,776,238 A | 12/1973 | Peyman et al. |
| 3,805,787 A | 4/1974 | Banko |
| 3,862,630 A | 1/1975 | Balamuth |
| 3,900,823 A | 8/1975 | Sokal et al. |
| 3,918,442 A | 11/1975 | Nikolaev et al. |
| 3,956,826 A | 5/1976 | Perdreaux, Jr. |
| 4,156,187 A | 5/1979 | Murry et al. |
| 4,200,106 A | 4/1980 | Douvas et al. |

(Continued)

FOREIGN PATENT DOCUMENTS

CN    1640365 A    7/2005

(Continued)

OTHER PUBLICATIONS

International Search Report for PCT/US08/57432, Nov. 3, 2008 (7 pages).

(Continued)

*Primary Examiner* — Ryan Severson
*Assistant Examiner* — Ashley Cronin
(74) *Attorney, Agent, or Firm* — K&L Gates, LLP

(57) ABSTRACT

A surgical instrument that may include a housing, a transducer engaged with the housing which can produce vibrations, and an end-effector engaged with the transducer. The surgical instrument can further include an adjustable sheath extending from the housing where the sheath is movable relative to the distal tip of the end-effector and where the distance between the distal tip of the sheath and the distal tip of the end-effector can be set such that the sheath can act as a depth stop. The sheath can be adjusted such that, when the distal tip of the sheath contacts the tissue or bone being incised, the surgeon can determine that the appropriate depth of the incision has been reached. In other embodiments, the end-effector can be moved with respect to the sheath in order to adjust the distance between the distal tip of the end-effector and the distal tip of the sheath.

23 Claims, 35 Drawing Sheets

U.S. PATENT DOCUMENTS

| | | |
|---|---|---|
| 4,445,063 A | 4/1984 | Smith |
| 4,491,132 A | 1/1985 | Aikins |
| 4,634,420 A | 1/1987 | Spinosa et al. |
| 4,640,279 A | 2/1987 | Beard |
| 4,708,127 A | 11/1987 | Abdelghani |
| 4,832,683 A | 5/1989 | Idemoto et al. |
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,922,902 A | 5/1990 | Wuchinich et al. |
| 4,981,756 A | 1/1991 | Rhandhawa |
| 5,026,387 A | 6/1991 | Thomas |
| 5,112,300 A | 5/1992 | Ureche |
| 5,123,903 A | 6/1992 | Quaid et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,184,605 A | 2/1993 | Grezeszykowski |
| 5,213,569 A | 5/1993 | Davis |
| 5,221,282 A | 6/1993 | Wuchinich |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,282,800 A | 2/1994 | Foshee et al. |
| D347,474 S | 5/1994 | Olson |
| 5,322,055 A | 6/1994 | Davison et al. |
| 5,324,299 A | 6/1994 | Davison et al. |
| 5,346,502 A | 9/1994 | Estabrook et al. |
| 5,366,466 A | 11/1994 | Christian et al. |
| D354,564 S | 1/1995 | Medema |
| 5,411,481 A | 5/1995 | Allen et al. |
| 5,419,761 A | 5/1995 | Narayanan et al. |
| 5,421,829 A | 6/1995 | Olichney et al. |
| 5,449,370 A | 9/1995 | Vaitekunas |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,562,609 A | 10/1996 | Brumbach |
| 5,562,610 A | 10/1996 | Brumbach |
| 5,601,601 A | 2/1997 | Tal et al. |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,733,074 A | 3/1998 | Stöck et al. |
| 5,741,226 A | 4/1998 | Strukel et al. |
| 5,810,859 A | 9/1998 | DiMatteo et al. |
| 5,827,323 A | 10/1998 | Klieman et al. |
| 5,828,160 A | 10/1998 | Sugishita |
| 5,843,109 A | 12/1998 | Mehta et al. |
| 5,879,364 A | 3/1999 | Bromfield et al. |
| 5,893,835 A | 4/1999 | Witt et al. |
| 5,897,569 A | 4/1999 | Kellogg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,989,274 A | 11/1999 | Davison et al. |
| 5,989,275 A | 11/1999 | Estabrook et al. |
| 5,993,972 A | 11/1999 | Reich et al. |
| 6,033,375 A | 3/2000 | Brumbach |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,113,594 A | 9/2000 | Savage |
| 6,139,320 A | 10/2000 | Hahn |
| 6,152,902 A | 11/2000 | Christian et al. |
| 6,159,160 A | 12/2000 | Hsei et al. |
| 6,159,175 A | 12/2000 | Strukel et al. |
| 6,206,844 B1 | 3/2001 | Reichel et al. |
| 6,210,403 B1 | 4/2001 | Klicek |
| 6,214,023 B1 | 4/2001 | Whipple et al. |
| 6,233,476 B1 | 5/2001 | Strommer et al. |
| 6,238,366 B1 | 5/2001 | Savage et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,352,532 B1 | 3/2002 | Kramer et al. |
| 6,379,320 B1 | 4/2002 | Lafon et al. |
| 6,383,194 B1 | 5/2002 | Pothula |
| 6,387,109 B1 | 5/2002 | Davison et al. |
| 6,391,042 B1 | 5/2002 | Cimino |
| 6,416,486 B1 | 7/2002 | Wampler |
| 6,423,073 B2 | 7/2002 | Bowman |
| 6,423,082 B1 | 7/2002 | Houser et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,316 B1 | 2/2003 | Nicholson et al. |
| 6,533,784 B2 | 3/2003 | Truckai et al. |
| 6,537,291 B2 | 3/2003 | Friedman et al. |
| 6,543,456 B1 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,676,660 B2 | 1/2004 | Wampler et al. |
| 6,678,621 B2 | 1/2004 | Wiener et al. |
| 6,679,899 B2 | 1/2004 | Wiener et al. |
| 6,682,544 B2 | 1/2004 | Mastri et al. |
| 6,716,215 B1 | 4/2004 | David et al. |
| 6,731,047 B2 | 5/2004 | Kauf et al. |

| | | |
|---|---|---|
| 6,733,506 B1 | 5/2004 | McDevitt et al. |
| 6,762,535 B2 | 7/2004 | Take et al. |
| 6,770,072 B1 | 8/2004 | Truckai et al. |
| 6,773,444 B2 | 8/2004 | Messerly |
| 6,786,382 B1 | 9/2004 | Hoffman |
| 6,786,383 B2 | 9/2004 | Stegelmann |
| 6,790,216 B1 | 9/2004 | Ishikawa |
| 6,802,843 B2 | 10/2004 | Truckai et al. |
| 6,828,712 B2 | 12/2004 | Battaglin et al. |
| 6,869,439 B2 | 3/2005 | White et al. |
| 6,875,220 B2 | 4/2005 | Du et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,926,716 B2 | 8/2005 | Baker et al. |
| 6,929,632 B2 | 8/2005 | Nita et al. |
| 6,929,644 B2 | 8/2005 | Truckai et al. |
| D509,589 S | 9/2005 | Wells |
| 6,945,981 B2 | 9/2005 | Donofrio et al. |
| D511,145 S | 11/2005 | Donofrio et al. |
| 6,976,969 B2 | 12/2005 | Messerly |
| 6,977,495 B2 | 12/2005 | Donofrio |
| 6,984,220 B2 | 1/2006 | Wuchinich |
| 7,011,657 B2 | 3/2006 | Truckai et al. |
| 7,041,088 B2 | 5/2006 | Nawrocki et al. |
| 7,041,102 B2 | 5/2006 | Truckai et al. |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,108,695 B2 | 9/2006 | Witt et al. |
| 7,112,201 B2 | 9/2006 | Truckai et al. |
| 7,118,564 B2 | 10/2006 | Ritchie et al. |
| 7,125,409 B2 | 10/2006 | Truckai et al. |
| 7,135,018 B2 | 11/2006 | Ryan et al. |
| 7,135,030 B2 | 11/2006 | Schwemberger et al. |
| 7,153,315 B2 | 12/2006 | Miller |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,163,548 B2 | 1/2007 | Stulen et al. |
| 7,169,146 B2 | 1/2007 | Truckai et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,204,820 B2 | 4/2007 | Akahoshi |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,309,849 B2 | 12/2007 | Truckai et al. |
| 7,311,709 B2 | 12/2007 | Truckai et al. |
| 7,331,410 B2 | 2/2008 | Yong et al. |
| 7,354,440 B2 | 4/2008 | Truckai et al. |
| 7,380,695 B2 | 6/2008 | Doll et al. |
| 7,381,209 B2 | 6/2008 | Truckai et al. |
| 7,390,317 B2 | 6/2008 | Taylor et al. |
| 7,408,288 B2 | 8/2008 | Hara |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,472,815 B2 | 1/2009 | Shelton, IV et al. |
| 7,479,148 B2 | 1/2009 | Beaupre |
| 7,479,160 B2 | 1/2009 | Branch et al. |
| 7,503,893 B2 | 3/2009 | Kucklick |
| 7,534,243 B1 | 5/2009 | Chin et al. |
| D594,983 S | 6/2009 | Price et al. |
| 7,567,012 B2 | 7/2009 | Namikawa |
| D618,797 S | 6/2010 | Price et al. |
| 7,751,115 B2 | 7/2010 | Song |
| 7,770,774 B2 | 8/2010 | Mastri et al. |
| 7,780,659 B2 | 8/2010 | Okada et al. |
| D631,965 S | 2/2011 | Price et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0016592 A1* | 2/2002 | Branch et al. .................. 606/61 |
| 2002/0019649 A1 | 2/2002 | Sikora et al. |
| 2002/0022836 A1 | 2/2002 | Goble et al. |
| 2002/0049464 A1* | 4/2002 | Donofrio et al. ............. 606/169 |
| 2002/0077550 A1 | 6/2002 | Rabiner et al. |
| 2002/0156493 A1 | 10/2002 | Houser et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2004/0030254 A1 | 2/2004 | Babaev |
| 2004/0047485 A1 | 3/2004 | Sherrit et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0122441 A1* | 6/2004 | Muratsu ....................... 606/102 |
| 2004/0199193 A1 | 10/2004 | Hayashi et al. |
| 2004/0204728 A1 | 10/2004 | Haefner |
| 2004/0260300 A1 | 12/2004 | Gorensek et al. |
| 2005/0049546 A1 | 3/2005 | Messerly et al. |
| 2005/0143769 A1 | 6/2005 | White et al. |
| 2005/0149108 A1 | 7/2005 | Cox |
| 2005/0149159 A1* | 7/2005 | Andreas et al. .............. 623/1.11 |
| 2005/0165345 A1 | 7/2005 | Laufer et al. |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |
| 2005/0261588 A1 | 11/2005 | Makin et al. |
| 2005/0288659 A1 | 12/2005 | Kimura et al. |
| 2006/0030797 A1 | 2/2006 | Zhou et al. |
| 2006/0063130 A1 | 3/2006 | Hayman et al. |
| 2006/0079878 A1 | 4/2006 | Houser |
| 2006/0084963 A1 | 4/2006 | Messerly |
| 2006/0190034 A1 | 8/2006 | Nishizawa et al. |
| 2006/0211943 A1 | 9/2006 | Beaupre |
| 2006/0235306 A1 | 10/2006 | Cotter et al. |
| 2006/0253050 A1 | 11/2006 | Yoshimine et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0060915 A1 | 3/2007 | Kucklick |
| 2007/0063618 A1 | 3/2007 | Bromfield |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0249941 A1 | 10/2007 | Salehi et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |

| | | | |
|---|---|---|---|
| 2009/0030439 A1 | 1/2009 | Stulen | |
| 2009/0036911 A1 | 2/2009 | Stulen | |
| 2009/0036912 A1 | 2/2009 | Wiener et al. | |
| 2009/0036913 A1 | 2/2009 | Wiener et al. | |
| 2009/0036914 A1 | 2/2009 | Houser | |
| 2009/0076506 A1 | 3/2009 | Baker | |
| 2009/0082716 A1 | 3/2009 | Akahoshi | |
| 2009/0105750 A1 | 4/2009 | Price et al. | |
| 2009/0118802 A1 | 5/2009 | Mioduski et al. | |
| 2009/0143795 A1 | 6/2009 | Robertson | |
| 2009/0143796 A1 | 6/2009 | Stulen et al. | |
| 2009/0143806 A1 | 6/2009 | Witt et al. | |
| 2010/0036370 A1 | 2/2010 | Mirel et al. | |
| 2010/0036405 A1 | 2/2010 | Giordano et al. | |
| 2010/0158307 A1 | 6/2010 | Kubota et al. | |
| 2010/0179577 A1 | 7/2010 | Houser | |
| 2010/0187283 A1 | 7/2010 | Crainich et al. | |
| 2010/0298743 A1 | 11/2010 | Nield et al. | |
| 2010/0298851 A1 | 11/2010 | Nield | |
| 2010/0331869 A1 | 12/2010 | Voegele et al. | |
| 2010/0331870 A1 | 12/2010 | Wan et al. | |
| 2010/0331871 A1 | 12/2010 | Nield et al. | |
| 2010/0331872 A1 | 12/2010 | Houser et al. | |
| 2011/0015627 A1 | 1/2011 | DiNardo et al. | |
| 2011/0015631 A1 | 1/2011 | Wiener et al. | |
| 2011/0015660 A1 | 1/2011 | Wiener et al. | |
| 2011/0082486 A1 | 4/2011 | Messerly et al. | |
| 2011/0087212 A1 | 4/2011 | Aldridge et al. | |
| 2011/0087213 A1 | 4/2011 | Messerly et al. | |
| 2011/0087214 A1 | 4/2011 | Giordano et al. | |
| 2011/0087215 A1 | 4/2011 | Aldridge et al. | |
| 2011/0087216 A1 | 4/2011 | Aldridge et al. | |
| 2011/0087217 A1 | 4/2011 | Yates et al. | |
| 2011/0087256 A1 | 4/2011 | Wiener et al. | |
| 2011/0125175 A1 | 5/2011 | Stulen et al. | |
| 2011/0196286 A1 | 8/2011 | Robertson et al. | |
| 2011/0196287 A1 | 8/2011 | Robertson et al. | |
| 2011/0196398 A1 | 8/2011 | Robertson et al. | |
| 2011/0196399 A1 | 8/2011 | Robertson et al. | |
| 2011/0196400 A1 | 8/2011 | Robertson et al. | |
| 2011/0196401 A1 | 8/2011 | Robertson et al. | |
| 2011/0196402 A1 | 8/2011 | Robertson et al. | |
| 2011/0196403 A1 | 8/2011 | Robertson et al. | |
| 2011/0196404 A1 | 8/2011 | Dietz et al. | |
| 2011/0196405 A1 | 8/2011 | Dietz | |

FOREIGN PATENT DOCUMENTS

| | | |
|---|---|---|
| EP | 0443256 A1 | 8/1991 |
| EP | 0456470 A1 | 11/1991 |
| EP | 0482195 B1 | 4/1992 |
| EP | 0482195 B1 | 1/1996 |
| EP | 0612570 B1 | 6/1997 |
| EP | 0908148 B1 | 1/2002 |
| EP | 1199044 B1 | 12/2005 |
| EP | 1844720 A1 | 10/2007 |
| EP | 1862133 A1 | 12/2007 |
| EP | 1974771 A1 | 10/2008 |
| EP | 1832259 B1 | 6/2009 |
| EP | 2074959 A1 | 7/2009 |
| GB | 2032221 A | 4/1980 |
| WO | WO 92/22259 A2 | 12/1992 |
| WO | WO 98/37815 A1 | 9/1998 |
| WO | WO 01/54590 A1 | 8/2001 |
| WO | WO 2005/122917 A1 | 12/2005 |
| WO | WO 2006/042210 A2 | 4/2006 |
| WO | WO 2006/129465 A1 | 12/2006 |
| WO | WO 2007/047531 A2 | 4/2007 |
| WO | WO 2007/143665 A2 | 12/2007 |
| WO | WO 2009/018406 A2 | 2/2009 |
| WO | WO 2009/027065 A1 | 3/2009 |

OTHER PUBLICATIONS

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
U.S. Appl. No. 11/881,654, filed Jul. 27, 2007.
U.S. Appl. No. 11/888,171, filed Jul. 31, 2007.
U.S. Appl. No. 11/998,758, filed Nov. 30, 2007.
U.S. Appl. No. 11/881,662, filed Jul. 27, 2007.
U.S. Appl. No. 11/888,222, filed Jul. 31, 2007.
U.S. Appl. No. 12/245,158, filed Oct. 3, 2008.
U.S. Appl. No. 29/292,295, filed Oct. 5, 2007.
U.S. Appl. No. 11/998,543, filed Nov. 30, 2007.
U.S. Appl. No. 29/327,737, filed Nov. 12, 2008.
U.S. Appl. No. 12/274,884, filed Nov. 20, 2008.
Technology Overview, printed from www.harmonicscaipel.com, Internet site, website accessed on Jun. 13, 2007, (3 pages).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (date unknown).
Lim et al., "A Review of Mechanism Used in Laparoscopic Surgical Instruments," Mechanism and Machine Theory, vol. 38, pp. 1133-1147, (2003).
AST Products, Inc., "Principles of Video Contact Angle Analysis," 20 pages, (2006).
U.S. Appl. No. 12/469,293, filed May 20, 2009.
U.S. Appl. No. 12/469,308, filed May 20, 2009.
U.S. Appl. No. 12/503,769, filed Jul. 15, 2009.
U.S. Appl. No. 12/503,770, filed Jul. 15, 2009.
U.S. Appl. No. 12/503,766, filed Jul. 15, 2009.
U.S. Appl. No. 12/490,906, filed Jun. 24, 2009.
U.S. Appl. No. 12/490,922, filed Jun. 24, 2009.
U.S. Appl. No. 12/490,933, filed Jun. 24, 2009.
U.S. Appl. No. 12/490,948, filed Jun. 24, 2009.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 12/732,702, filed Mar. 26, 2010.
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al, "Thermal Imaging in Surgery," p. 19-3, in *Medical Infrared Imaging*, N. A. Diakides and J. D. Bronzino, Eds. (2008).
U.S. Appl. No. 12/896,351, filed Oct. 1, 2010.
U.S. Appl. No. 12/896,411, filed Oct. 1, 2010.
U.S. Appl. No. 12/896,420, filed Oct. 1, 2010.

\* cited by examiner

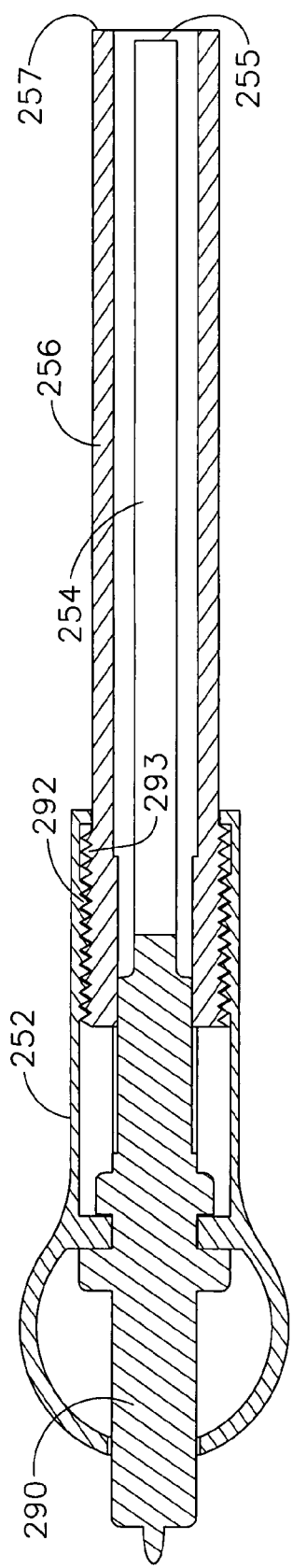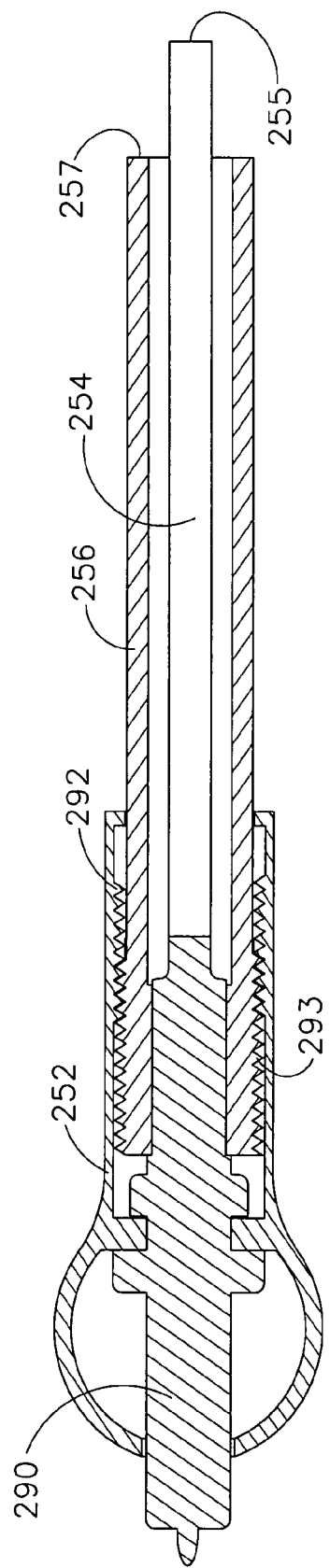

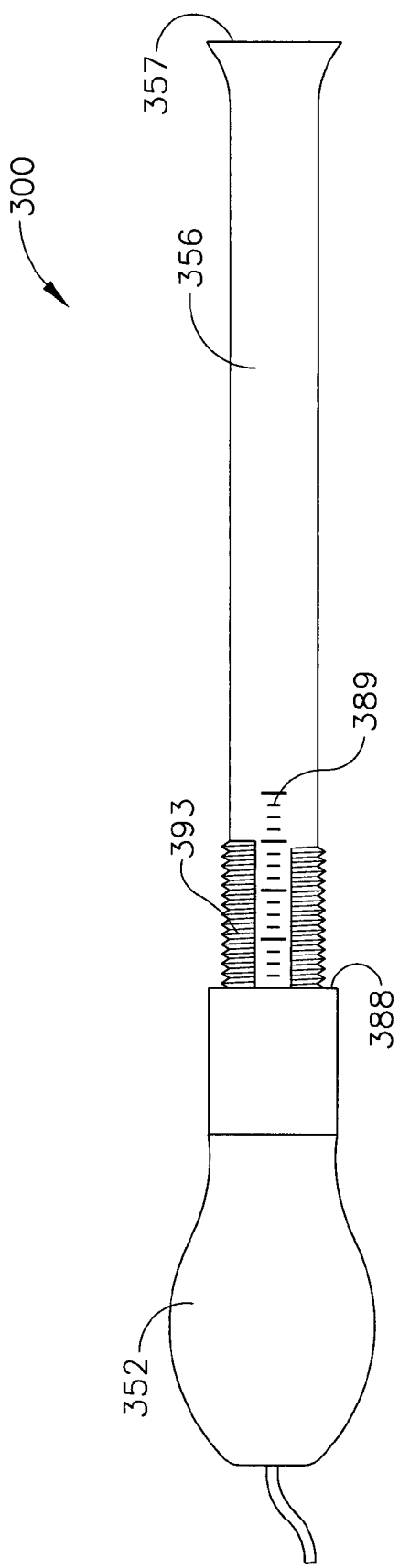
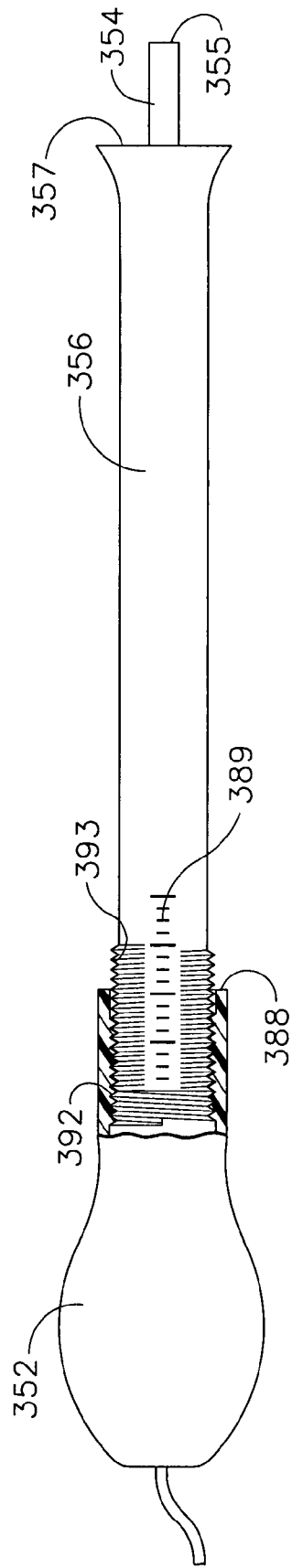
FIG. 22
FIG. 23

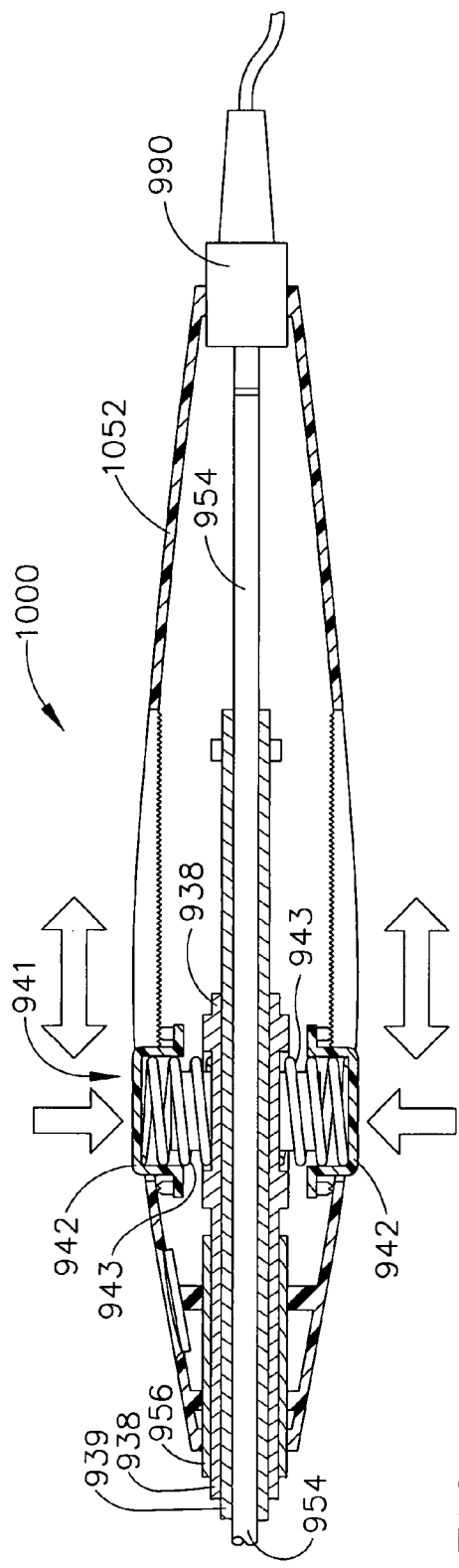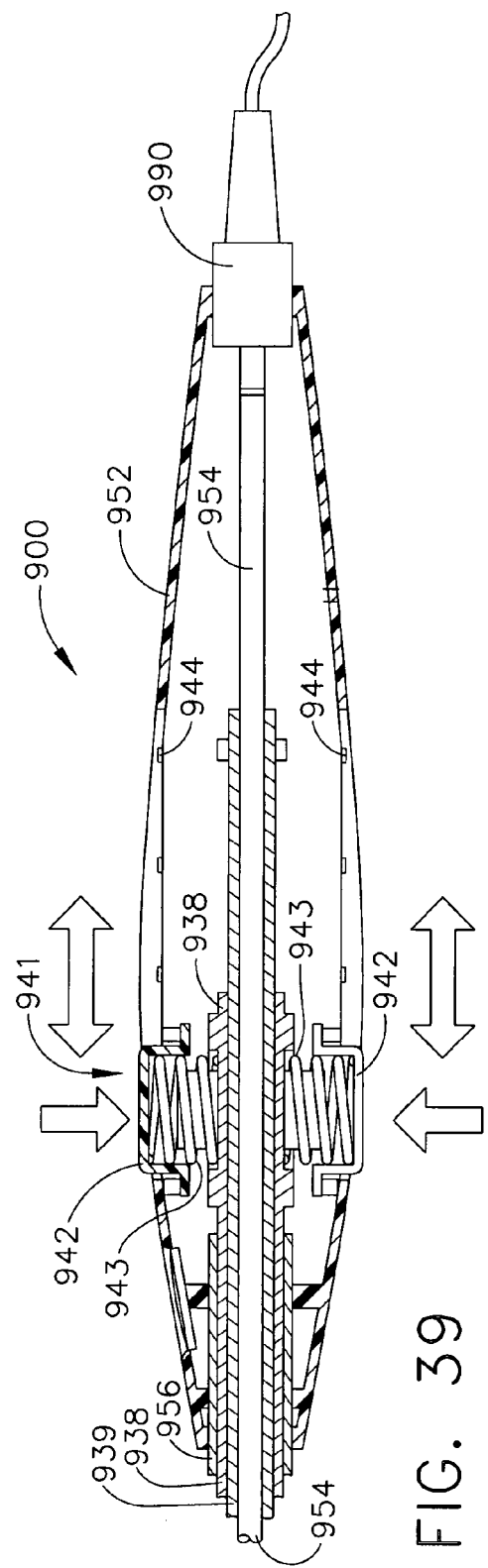
FIG. 38
FIG. 39

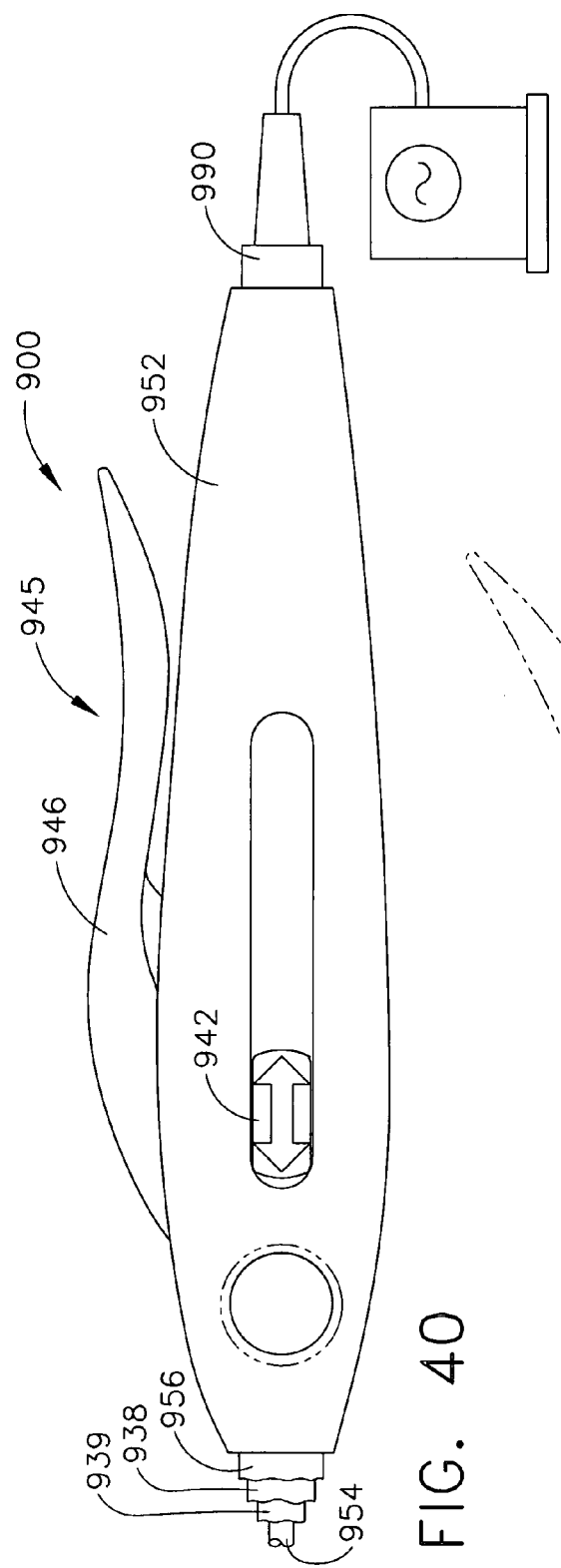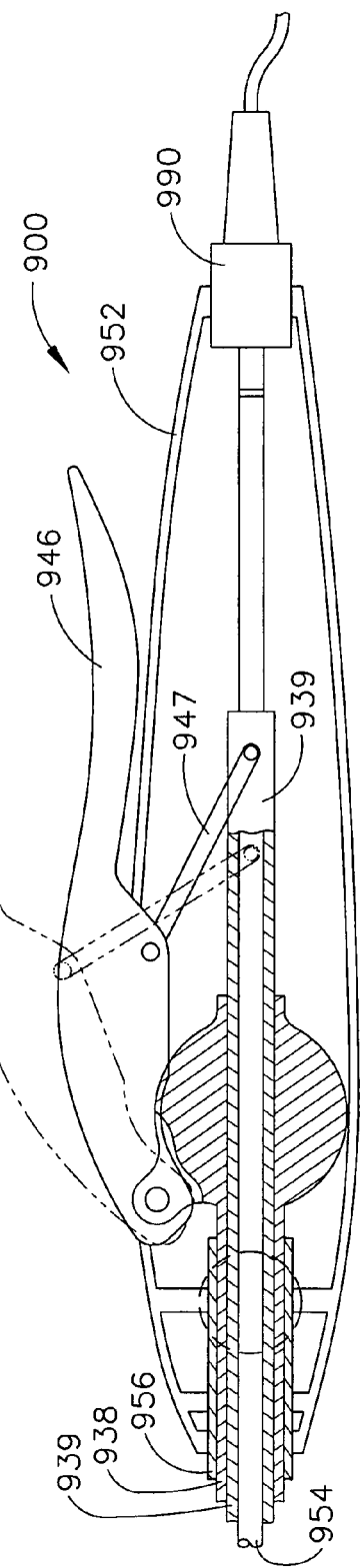
FIG. 40
FIG. 41

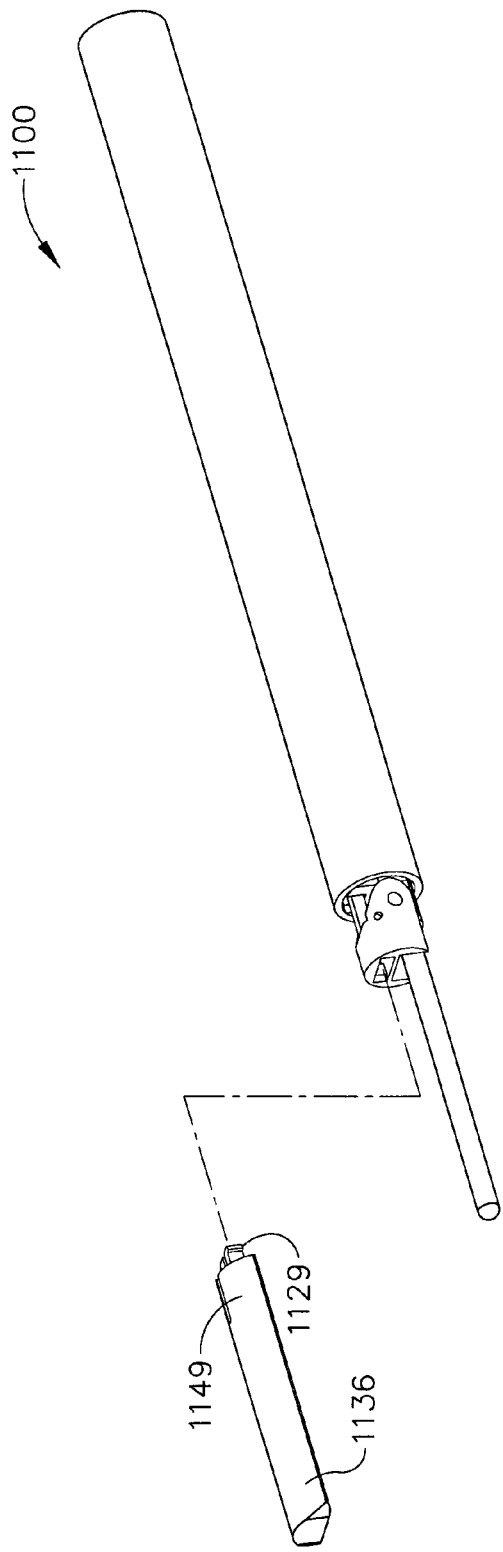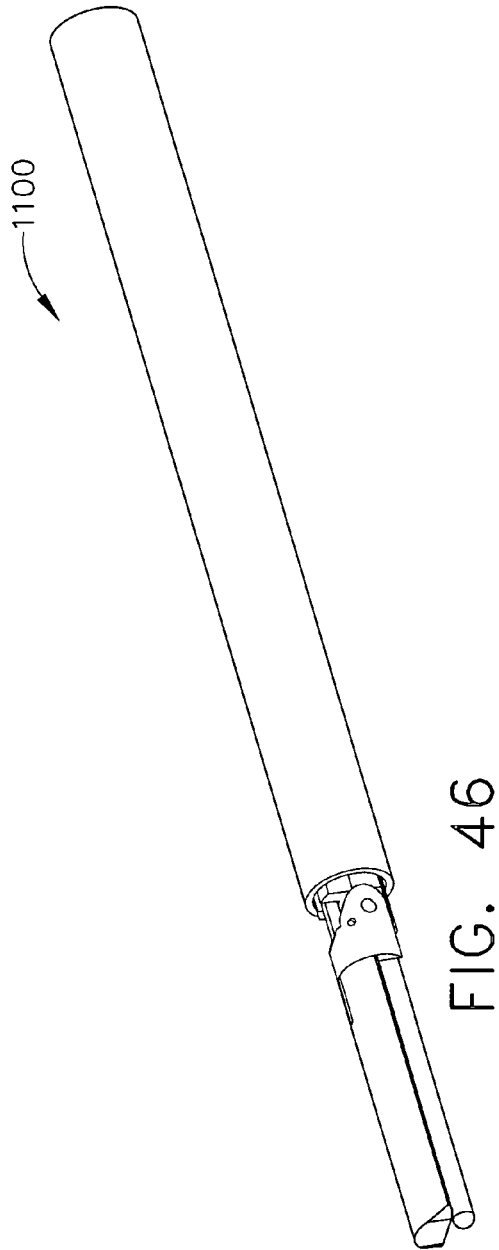

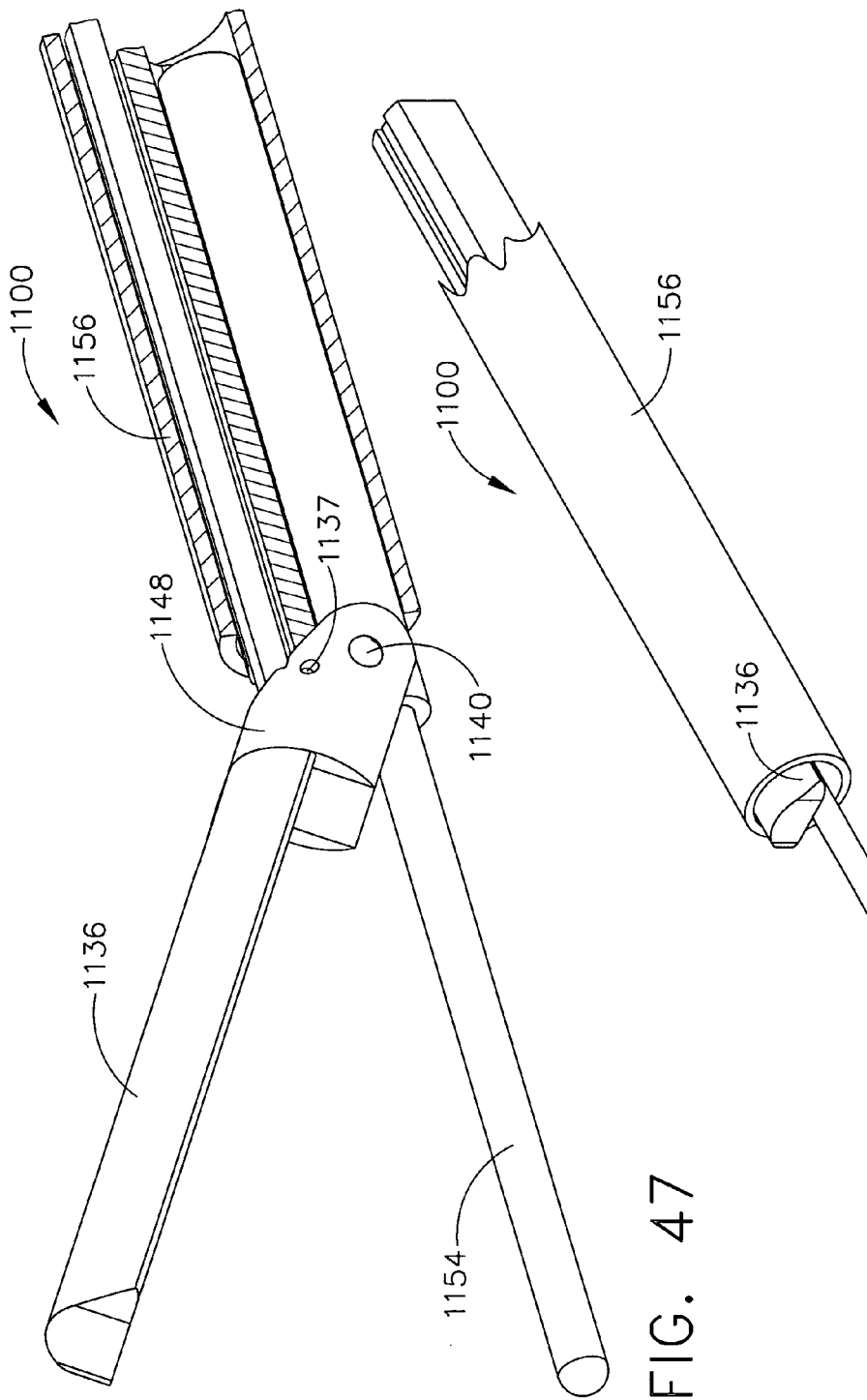

SURGICAL INSTRUMENTS

CROSS-REFERENCE TO RELATED APPLICATIONS

The present application is related to the following commonly-owned U.S. patent applications filed concurrently herewith, and which are hereby incorporated by reference in their entirety:

(1) U.S. patent application Ser. No. 11/726,625, entitled SURGICAL INSTRUMENTS;

(2) U.S. patent application Ser. No. 11/726,760, entitled ULTRASONIC SURGICAL INSTRUMENTS; and (3) U.S. patent application Ser. No. 11/726,621, entitled ULTRASONIC SURGICAL INSTRUMENTS AND CARTILAGE BONE SHAPING BLADES THEREFOR.

BACKGROUND

1. Field on the Invention

The present invention generally relates to ultrasonic surgical instruments and, more particularly, to harmonic scalpels for cutting bone and for cutting and/or coagulating tissue, for example.

2. Description of the Related Art

Ultrasonic surgical instruments can be used for the safe and effective treatment of many medical conditions. Generally, ultrasonic surgical instruments can be used to cut and/or coagulate organic tissue, for example, using energy in the form of ultrasonic vibrations, i.e., mechanical vibrations transmitted to a surgical end-effector at ultrasonic frequencies. These ultrasonic vibrations, when transmitted to organic tissue at suitable energy levels and using a suitable end-effector, may be used to cut and/or coagulate the tissue. Such instruments may be used for open procedures or minimally invasive procedures, such as endoscopic or laparoscopic procedures, for example, wherein the end-effector is passed through a trocar to reach a surgical site.

Although ultrasonic surgical instruments can perform their intended function remarkably well, the energy and vibrations created by these instruments is significant and, if not properly controlled, can unintentionally cause damage to tissue and/or bone surrounding the surgical site. As a result, several safety features have been developed to prevent, or at least reduce the possibility of, such damage from occurring. For example, some surgical instruments have been developed which include sheaths that extend around at least a portion of the end-effector. In use, these sheaths can prevent portions of the end-effector from unintentionally contacting tissue or bone surrounding the surgical site. However, these sheaths can block the surgeon's view of the surgical site, for example. As a result, the surgeon may not be able to readily ascertain the depth of their incisions and make corrective adjustments. What is needed is an improvement over the foregoing.

SUMMARY

In at least one form of the invention, a surgical instrument can include a housing, a transducer engaged with the housing where the transducer is configured to produce vibrations, and an end-effector engaged with the transducer. In various embodiments, the end-effector can define an axis and a distal tip where the distal tip is movable along the axis by vibrations produced by the transducer. In at least one embodiment, the surgical instrument can further include an adjustable sheath extending from the housing where the sheath is movable relative to the distal tip of the end-effector. In these embodiments, the distance between the distal tip of the sheath and the distal tip of the end-effector can be set such that the sheath can act as a depth stop. More particularly, the sheath can be adjusted such that, when the distal tip of the sheath contacts the tissue or bone being incised, for example, the surgeon can readily determine that the appropriate depth of the incision has been reached. In other various embodiments, the end-effector can be moved with respect to the sheath in order to adjust the distance between the distal tip of the end-effector and the distal tip of the sheath.

In at least one form of the invention, a surgical instrument can include a sheath which is removably attached to the housing of the surgical instrument. In various embodiments, a kit can be provided which includes a plurality of sheaths where each sheath can have a different length and/or configuration. In at least one embodiment, the kit can include a first sheath and a second sheath where, when the first sheath is assembled to the housing, the distal tip of the end-effector and the distal tip of the first sheath define a first distance therebetween, and, when the second sheath is assembled to the housing, the distal tip of the end-effector and the distal tip of the second sheath define a second distance therebetween which is different than the first distance. In these embodiments, a surgeon can select a sheath from the kit such that the sheath, when its distal tip contacts the tissue or bone being incised, for example, allows the surgeon to readily determine that the desired depth of the incision has been reached.

In at least one form of the invention, a surgical instrument can include a housing, a transducer engaged with the housing where the transducer is configured to produce vibrations, and an end-effector engaged with the transducer. The end-effector can include a first treatment region, a second treatment region, and at least one indicium or demarcation on the end-effector configured to identify the first treatment region, for example. In at least one such embodiment, the first treatment region can include a cutting edge configured to cut tissue and the second treatment region can include an arcuate surface configured to cauterize or coagulate tissue where the at least one indicium or demarcation can allow a surgeon to readily identify such portions of the end-effector. Similarly, in at least one embodiment, the at least one indicium or demarcation can be configured to indicate which portions of the end-effector vibrate at a high intensity and which portions vibrate at a low intensity.

In at least one form of the invention, a surgical instrument can include a housing, a transducer engaged with the housing where the transducer is configured to produce vibrations, and an end-effector engaged with the transducer. The end-effector can further include a clamp having a jaw member and a pivot where the jaw member is rotatable with respect to the end-effector between an open position and a closed position about the pivot. In addition, the clamp can be translatable between a first position and a second position with respect to the distal tip of the end-effector. In these embodiments, the jaw member can be used, if desired, to hold tissue against the end-effector as it is being incised, for example, or, alternatively, the clamp can be translated away from the distal tip of the end-effector such that the end-effector can be used without the clamp. Such features allow the surgeon to use one instrument to perform various tasks where more than one instrument was previously required to perform the same tasks.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 18 is a cross-sectional view of the surgical instrument of FIG. 16 where the sheath is in a fully extended position;

FIG. 21 is a cross-sectional view of the surgical instrument of FIG. 16 where the sheath is in a retracted position;

FIG. 22 is a plan view of a surgical instrument in accordance with an alternative embodiment of the present invention having indicia on the sheath to indicate the distance between the distal tip of the sheath and the distal tip of the end-effector;

FIG. 23 is a partial cross-sectional view of the surgical instrument of FIG. 22;

FIG. 38 is a cross-sectional view of an alternative embodiment of an actuator in accordance with an embodiment of the present invention operably configured to extend and retract the clamp of the surgical instrument of FIG. 34;

FIG. 39 is a cross-sectional view of an actuator operably configured to extend and retract the clamp of the surgical instrument of FIG. 34;

FIG. 40 is a partial elevational view of the surgical instrument of FIG. 34 illustrating a second actuator configured to move the jaw member of the surgical instrument between an open and closed position;

FIG. 41 is a cross-sectional view of the surgical instrument of FIG. 34 illustrating the second actuator of FIG. 40;

FIG. 45 is an exploded assembly view of a surgical instrument in accordance with an alternative embodiment of the present invention having a removably attachable jaw member;

FIG. 46 is a perspective view of the surgical instrument of FIG. 45;

FIG. 47 is a perspective view of the clamp of the surgical instrument of FIG. 45 where the jaw member is in an open position and where some components are shown in cross-section for clarity;

FIG. 48 is a partial perspective view of the clamp of the surgical instrument of FIG. 45 in a retracted position;

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 1:
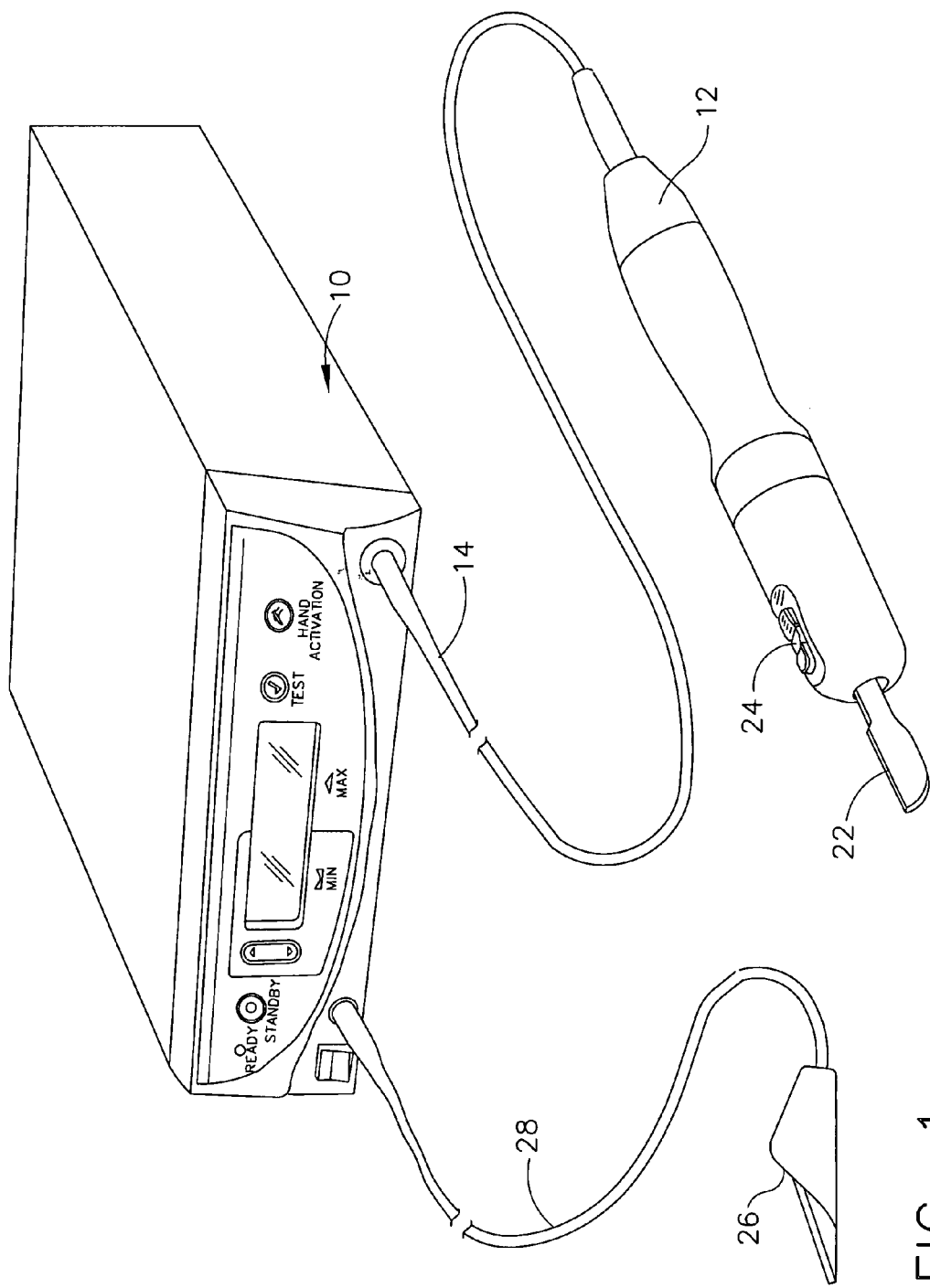
FIG. 1 is a perspective view of a ultrasonic surgical instrument operably connected to a signal generator.

As indicated above, ultrasonic surgical instruments can be used to cut, cauterize, and/or coagulate organic tissue, for example, using energy in the form of ultrasonic vibrations, i.e., mechanical vibrations transmitted to a surgical end-effector at ultrasonic frequencies. Examples of ultrasonic surgical instruments are disclosed in U.S. Pat. Nos. 5,322,055, 5,954,736, 6,278,218, 6,283,981, 6,309,400, and 6,325,811, the disclosures of which are incorporated by reference herein in their entirety. In various embodiments, an ultrasonic signal generator can be provided which produces a desired electrical signal and can be connected to a handpiece of the surgical instrument by a cable. A suitable generator is available as model number GEN04, from Ethicon Endo-Surgery, Inc., Cincinnati, Ohio. In one embodiment, referring to FIG. 1, the electrical signal, i.e., the drive current, can be transmitted from generator 10 to hand piece 12 through cable 14.

Figure 2:
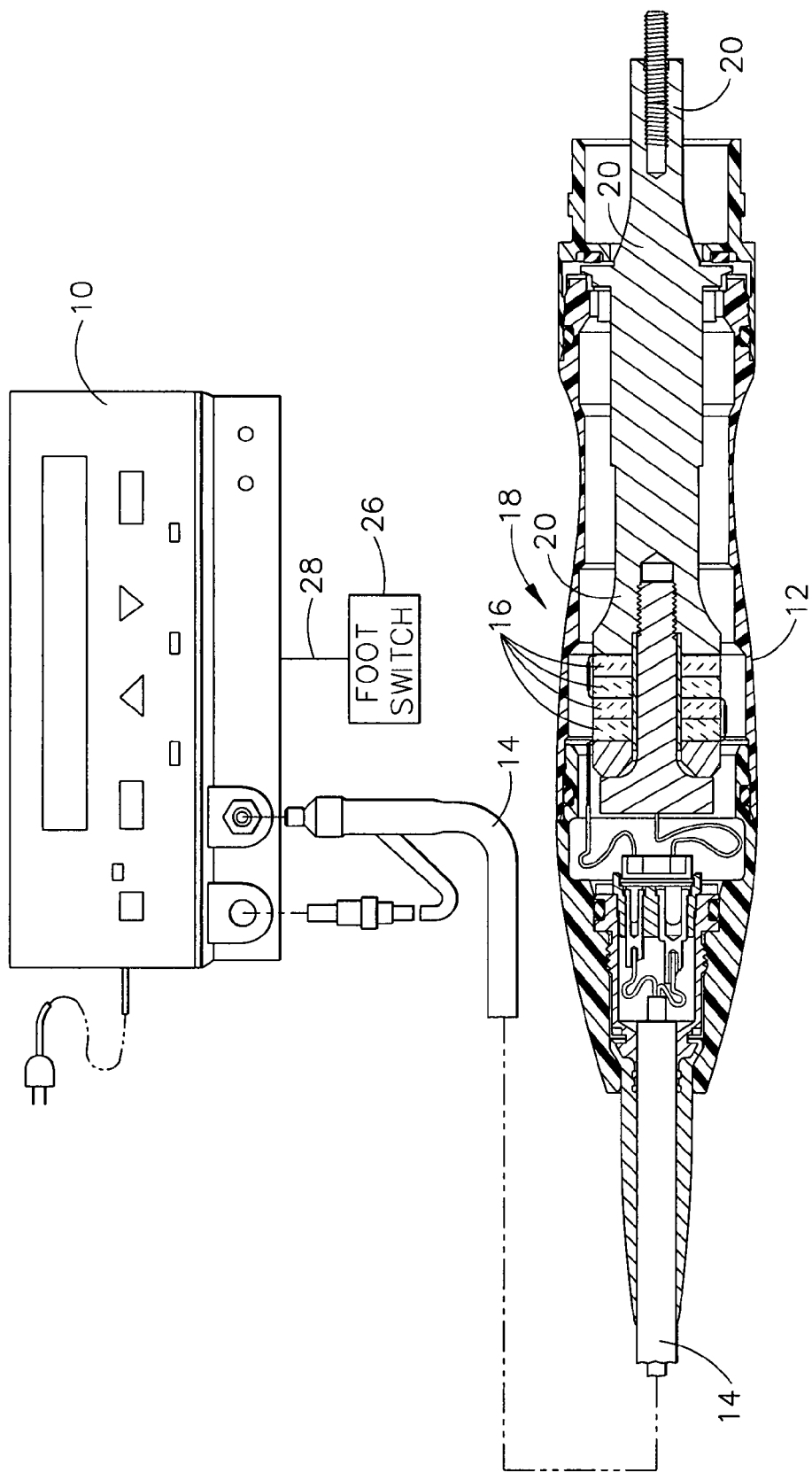
FIG. 2 is a cross-sectional view of the ultrasonic surgical instrument of FIG. 1.

Referring to FIG. 2, handpiece 12 can include transducer 18 comprising piezoceramic elements 16, for example, which can be configured to convert the drive current into mechanical vibrations. More particularly, the drive current can cause disturbances in elements 16 in the form of repeated displacements which can, in turn, cause elements 16 to expand and contract in a continuous manner along a voltage gradient, or axis, producing longitudinal waves of ultrasonic energy along this axis. In various embodiments, elements 16 can produce vibrations transverse to, or in a torsional manner about, the longitudinal axis. Piezoceramic elements 16 can be fabricated from any suitable material such as lead zirconate-titanate, lead meta-niobate, lead titanate, or other piezoelectric crystal materials, for example. In various embodiments, elements 16 can include magnetostrictive elements including, for example, alloys comprised of iron, cobalt and rare earth elements including nickel, vanadium, dysprosium, and terbium. Magnetostriction is a property of ferromagentic materials that causes the materials to change shape when they are subjected to a magnetic field. Magnetostrictive elements are further described in U.S. Pat. No. 7,157,058, the disclosure of which is incorporated by reference herein in its entirety. In any event, transducer 18 can be comprised of any mechanism or material which can produce the required vibratory motion to end-effector 22 as described below.

In use, the longitudinal waves created by transducer 18 can produce longitudinal vibratory movement of waveguide 20 and end-effector 22 mounted thereto. In at least one embodiment, the drive current can include an alternating current defined by a substantially sinusoidal frequency which, owing to the excitation of elements 16 described above, causes waveguide 20 and end-effector 22 to vibrate longitudinally in a substantially sinusoidal manner. In various embodiments, transducer 18 can be configured such that waveguide 20 and end-effector 22 are vibrated at a preselected resonant frequency. In at least one such embodiment, piezoceramic elements 16 can be driven at ultrasonic frequencies including frequencies between approximately 50,000 and approximately 60,000 cycles per second, for example. In other embodiments, elements 16 can be driven at frequency greater than or equal to approximately 20,000 cycles per second. In addition to the above, the magnitude of the drive current voltage can dictate the magnitude of the displacement of end-effector 22.

When piezoceramic elements 16 are energized, a vibratory motion standing wave is generated through transducer 18, waveguide 20 and end-effector 22. The amplitude of the vibratory motion at any point along these components may depend upon the location at which the vibratory motion is measured. For example, at some locations along wave guide 20 and end-effector 22, the vibratory motion may be at a higher intensity or amplitude and, at other locations, at a lower intensity or amplitude. At some locations, the vibratory motion is zero, or substantially zero. A minimum or zero point in the vibratory motion standing wave is generally referred to as a node whereas a maximum or peak in the standing wave is generally referred to as an anti-node. The distance between an anti-node and an adjacent node is approximately one-quarter wavelength of the standing wave frequency, i.e., $\lambda/4$. These nodal locations also correspond to the relative maximum stress locations in the system whereas the anti-nodes correspond to relative minimum stress locations.

In order to transmit the standing wave from transducer 18 to waveguide 20, waveguide 20 must be acoustically coupled to transducer 18, i.e., they must be attached in such a way that mechanical vibrations produced by transducer 18 are transmitted into wave guide 20. Similarly, in order to transmit these vibrations to the distal tip of end-effector 22, waveguide 20 and end-effector 22 must also be acoustically coupled if manufactured as separate components. In preferred embodiments, such couplings are configured to substantially coincide with the anti-nodes of the standing wave such that little, if any, vibratory stress is present at the couplings. In these embodiments, as a result, the possibility of transducer 18, waveguide 20 and end-effector 22 becoming decoupled is reduced.

In various embodiments, transducer 18, waveguide 20 and end-effector 22 can comprise an assembly which can be driven at, or close to, its resonant, or natural, frequency and amplify the motion initiated by transducer 18. In the illustrated embodiment, end-effector 22 comprises a blade which is integral with waveguide 20 and can be constructed from a material suitable for transmission of ultrasonic energy such as, for example, Ti6Al4V (an alloy of titanium including aluminum and vanadium), aluminum, stainless steel, or other known materials. Alternately, blade 22 may be manufactured as a separate component and can be comprised of a different material than waveguide 20, for example. In these embodiments, blade 22 and waveguide 20 can be coupled by a stud, a threaded connection or by any suitable process including welding, gluing, or any known methods, for example. In various embodiments, at least portions of the waveguide, blade and transducer can be comprised of a continuous material In order to operate the ultrasonic surgical system in an efficient manner, the frequency of the signal supplied to transducer 18 can be swept over a range of frequencies to locate the resonance frequency. In at least one embodiment, a switch, such as switch 24, on hand piece 12 can be manipulated to activate the signal sweep. Once the resonance frequency is found, generator 10 can lock onto the resonance frequency, monitor the transducer current to voltage phase angle, and adjust the drive current such that it drives the waveform and blade assembly at, or close to, the resonance frequency. In at least one embodiment, once the generator has locked onto the resonant frequency, an audio indicator, for example, can be communicated to the user to indicate the same. Once the resonant frequency of the system has been determined, the drive current can be immediately supplied to hand piece 12 and/or the drive current may be controlled by the operation of switch 24 located thereon, for example. In other embodiments, the drive current may be controlled by foot switch 26 which is connected to generator 10 by cable 28.

Figure 3:
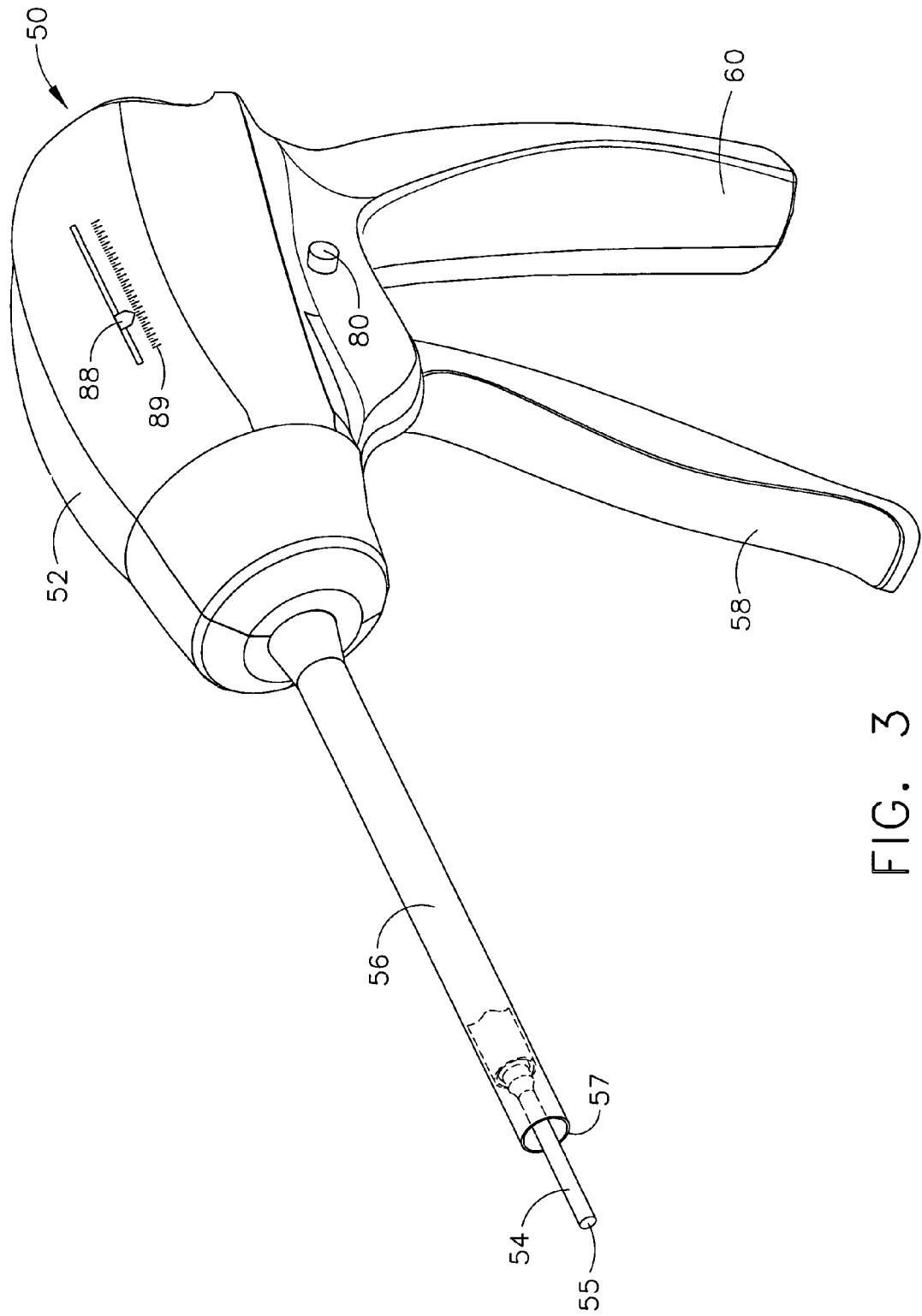
FIG. 3 is a perspective view of a surgical instrument in accordance with an embodiment of the present invention.

Referring to FIG. 3, surgical instrument 50 can include housing 52, end-effector 54 and adjustable sheath 56. In use, sheath 56 can act as a depth stop when a surgeon is incising tissue or bone, for example. More particularly, as the surgeon inserts end-effector 54 into the tissue or bone, the surgeon can force end-effector 54 therein until distal tip 57 of sheath 56 contacts the surface thereof. Once distal tip 57 of sheath 56 has contacted the surface of the tissue or bone, the surgeon will know that distal tip 55 of end-effector 54 has reached the desired depth therein. As a result, the likelihood of the surgeon inserting end-effector 54 into the tissue or bone beyond the desired depth is reduced. This feature is particularly useful in applications where the surgeon is required to plunge end-effector 54 into the tissue or bone. In one such embodiment, a surgeon may be required to create a pilot hole in a bone, such as a vertebral body, for example, before a screw is inserted into the bone. In various embodiments, sheath 56 can also substantially prevent end-effector 54 from accidentally contacting the tissue or bone surrounding the surgical site. Although sheath 56 is illustrated as entirely surrounding the perimeter of end-effector 54, other embodiments are envisioned where sheath 56 only partially surrounds the perimeter of end-effector 54.

Figure 4:
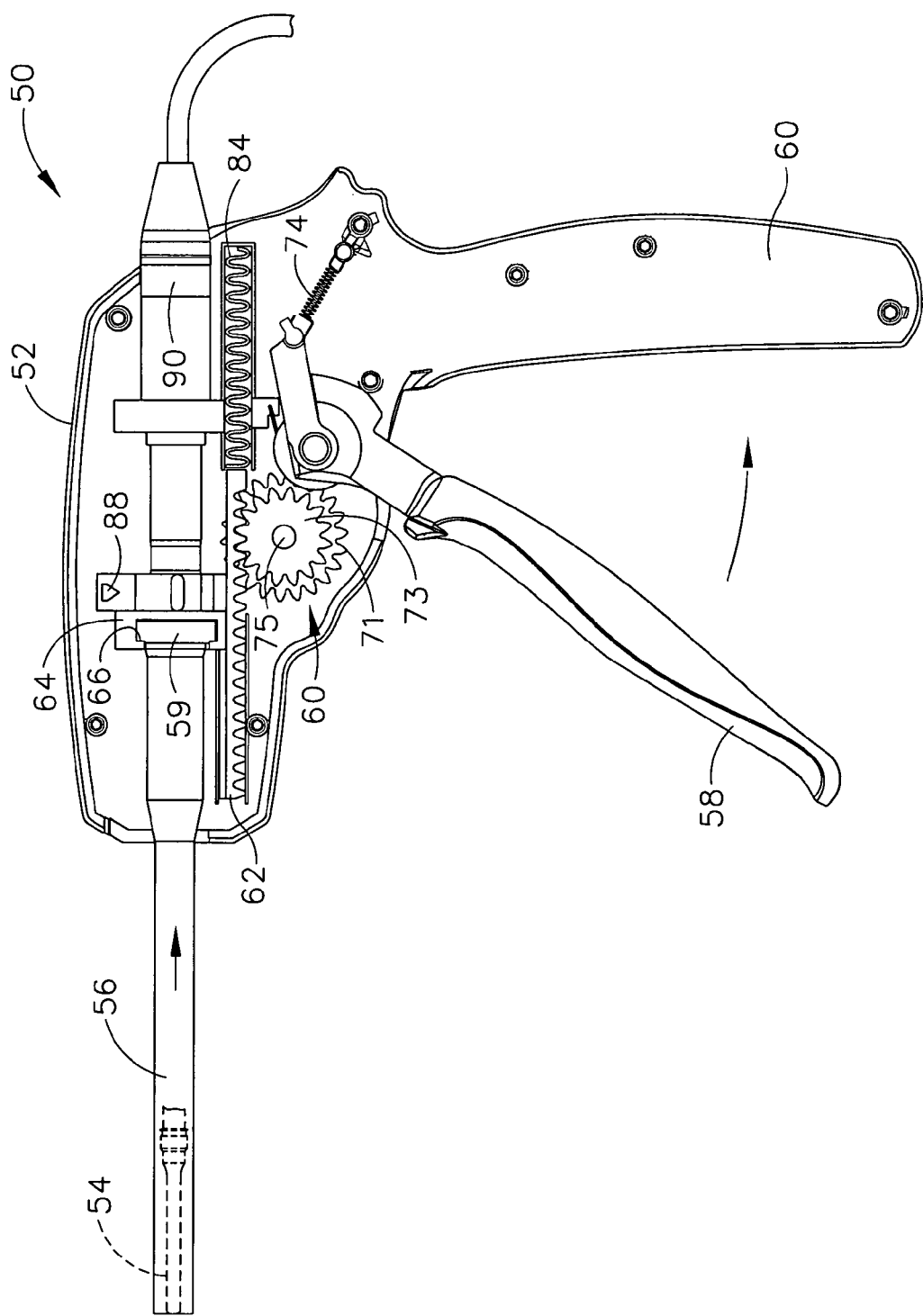
FIG. 4 is a partial cross-sectional view of the surgical instrument of FIG. 3 wherein the sheath of the surgical instrument is extended to cover the end-effector.

In various embodiments, as discussed in further detail below, the position of sheath 56 can be adjusted to change the distance between distal tip 55 of end-effector 54 and distal tip 57 of sheath 56. In at least one such embodiment, referring to FIGS. 4 and 5, sheath 56 can be operably engaged with actuator 58 such that, when actuator 58 is operated, distal tip 57 of sheath 56 is moved away from distal tip 55 of end-effector 54, for example. More particularly, referring to FIGS. 3-8 which illustrate the present embodiment, surgical instrument 50 can include ratchet mechanism 60 which, when operated by actuator 58, can move sheath 56 proximally with respect to distal tip 55 of end-effector 54 and uncover a treatment portion thereof. As a result, a surgeon, or other clinician, for example, may adjust the position of sheath 56 to suit the needs of a particular application by setting the distance between distal end 55 and distal end 57 such that end-effector 54 does not incise the tissue or bone deeper than desired.

Figure 5:
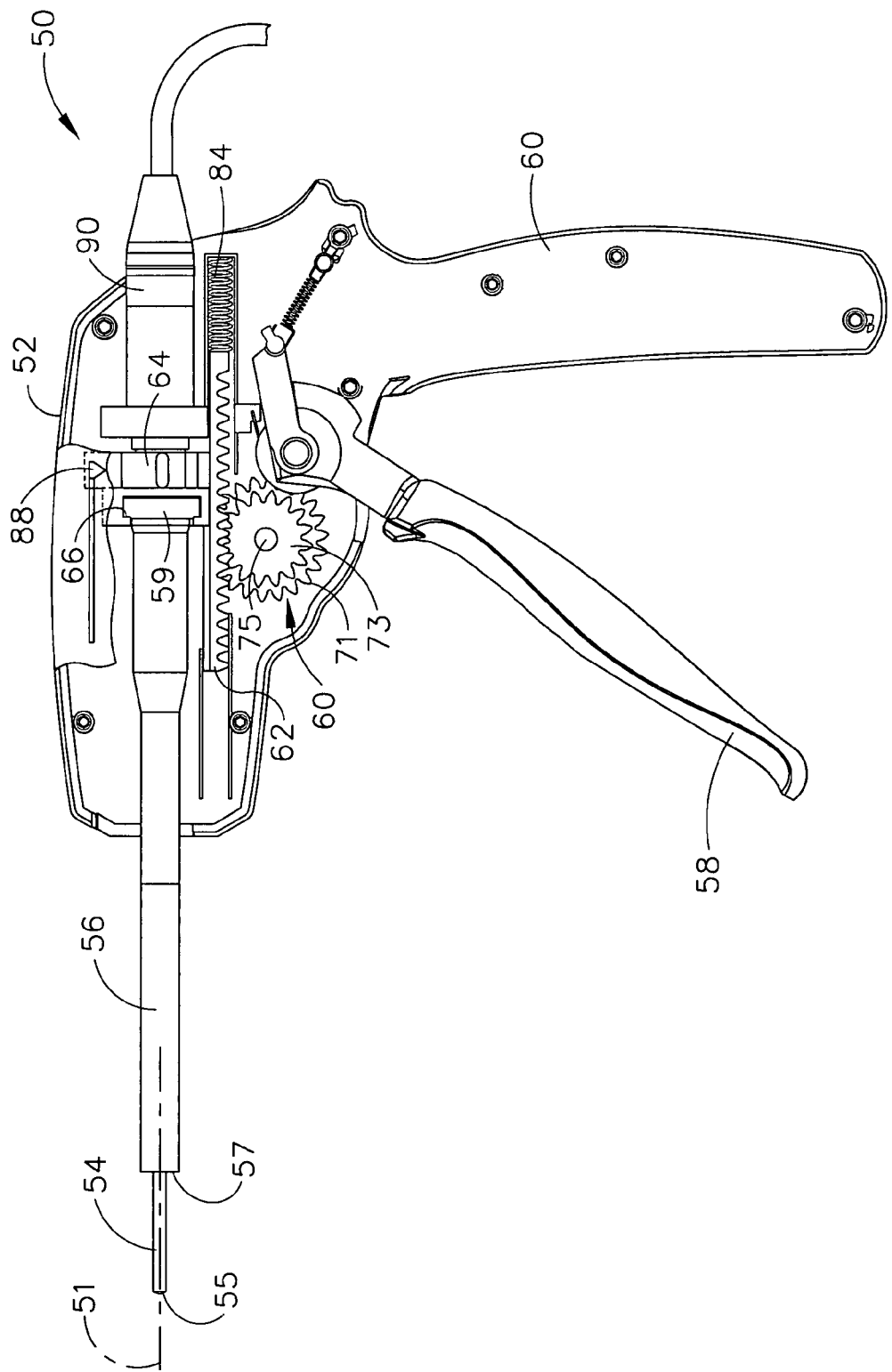
FIG. 5 is a partial cross-sectional view of the surgical instrument of FIG. 3 wherein the sheath has been retracted to uncover a portion of the end-effector.
Figure 6:
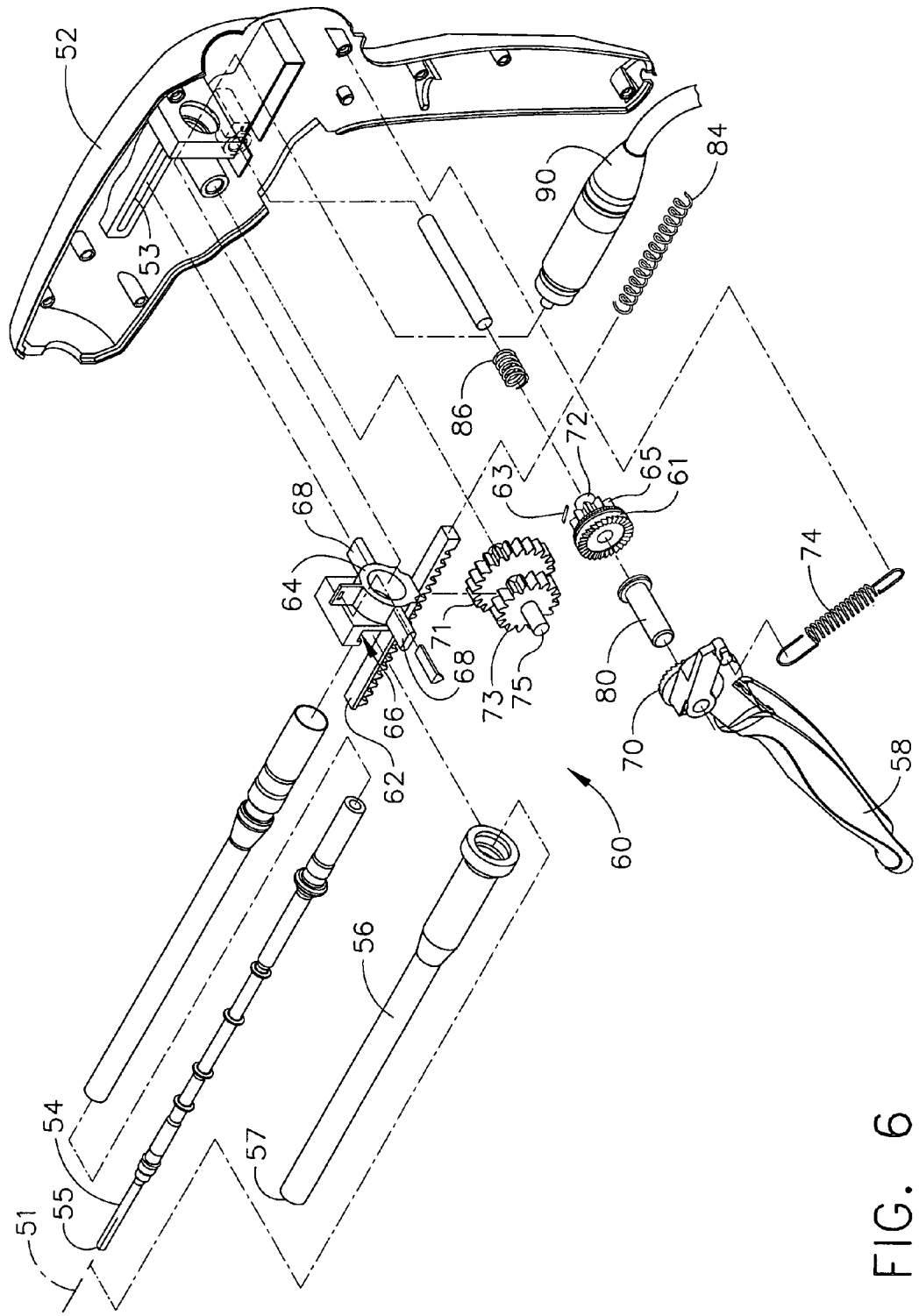
FIG. 6 is an exploded assembly view of the surgical instrument of FIG. 3.

Referring primarily to FIGS. 4-7, sheath 56 can be mounted to rack 62 via collar 64. In the present embodiment, sheath 56 can be fixedly retained, or press-fit, within slot 66 of collar 64 such there is substantially no relative translational or rotational movement therebetween. More particularly, sheath 56 can include flange 59 which is configured to be slid into slot 66 and retain sheath 56 to collar 64. In other embodiments, however, sheath 56 and collar 64 can be configured to permit relative rotational movement therebetween, for example. Referring to FIG. 6, collar 64 can include projections 68 extending therefrom which are sized and configured to be slidably retained within slots 53 of housing 52. As a result of projections 68, when rack 62 is moved relative to housing 52, as discussed in greater detail below, slots 53 can define the path of rack 62. In the present embodiment, slots 53 define a substantially linear path such that rack 62 is moved along, or parallel to, an axis defined by end-effector 54, i.e., axis 51 (FIG. 5). However, in other various embodiments, other paths, including non-linear paths, are contemplated.

Figure 7:
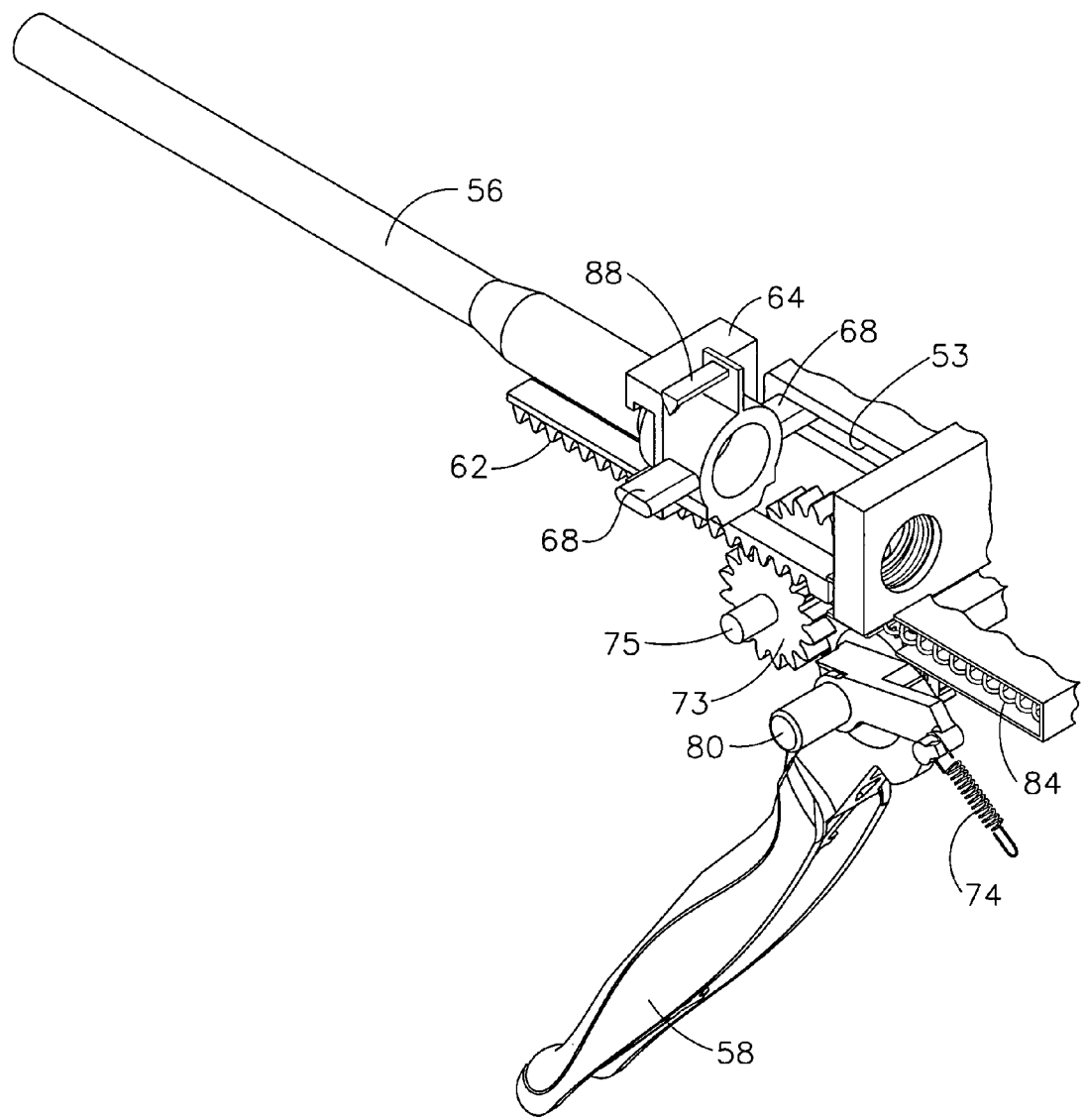
FIG. 7 is a perspective view of the ratchet mechanism and sheath of the surgical instrument of FIG. 3.
Figure 8:
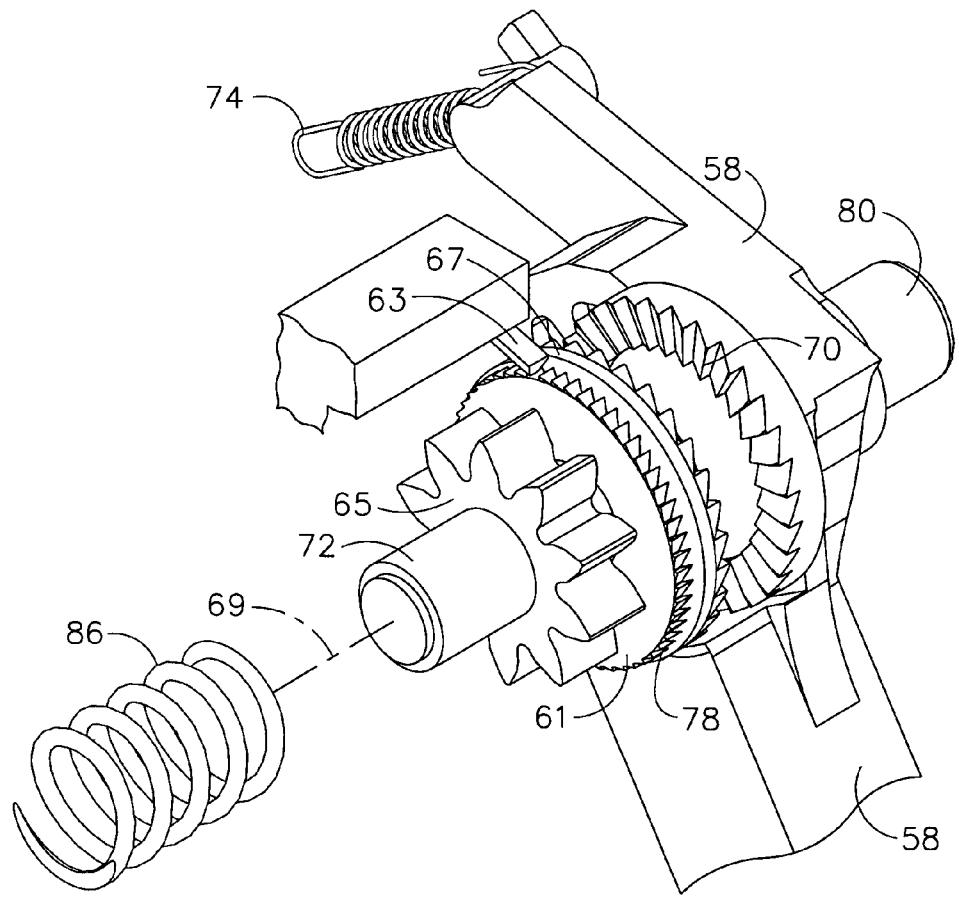
FIG. 8 is an exploded assembly view of portions of the ratchet mechanism of FIG. 7.

In order to move rack 62 relative to housing 52, in the present embodiment, actuator 58 can be engaged with ratchet mechanism 60 such that, when actuator 58 is moved toward handle 60, ratchet mechanism 60 slides rack 62 proximally with respect to distal tip 55 of end-effector 54. Referring primarily to FIGS. 7 and 8, ratchet mechanism 60 can include ratchet wheel 61, pawl 63, and drive gear 65. In the present embodiment, ratchet wheel 61 can include gear face 67 which is configured to engage gear face 70 of actuator 58 such that, when actuator 58 is moved toward handle 60, gear faces 67 and 70 drive ratchet wheel 61 about axis 69 (FIG. 8). In at least one embodiment, gear faces 67 and 70 can include teeth which are configured to mesh together when actuator 58 is rotated toward handle 60, as described above, but are also configured to permit relative sliding movement therebetween when actuator 58 is rotated in the opposite direction. More particularly, after actuator 58 has been brought into close opposition to handle 60, gear faces 67 and 70 can be configured such that, when actuator 58 is released, spring 74 can pull actuator 58 back into its starting position by dragging gear face 70 across gear face 67. After actuator 58 has been repositioned by spring 74, actuator 58 can again be pulled toward handle 60 to further rotate ratchet wheel 61.

Referring to FIG. 8, ratchet wheel 61 can be fixedly mounted to drive shaft 72 such that, when ratchet wheel 61 is rotated about axis 69 by actuator 58, drive shaft 72 is also rotated about axis 69. Drive gear 65 can also be fixedly mounted to drive shaft 72 such that, when ratchet wheel 61 is rotated, drive shaft 72 rotates drive gear 65. Referring primarily to FIG. 6, drive gear 65 can be operably engaged with large gear 71 such that the rotation of drive gear 65 rotates large gear 71. Large gear 71 can be fixedly mounted to pinion gear 73 via shaft 75 such that the rotation of large gear 71 rotates pinion gear 73. Referring to FIG. 6, pinion gear 73 can be operably engaged with rack 62 such that, when actuator 58 is operated, the gear train comprising drive gear 65, large gear 71 and pinion gear 73 is operated to slide rack 62 proximally as described above.

Figure 9:
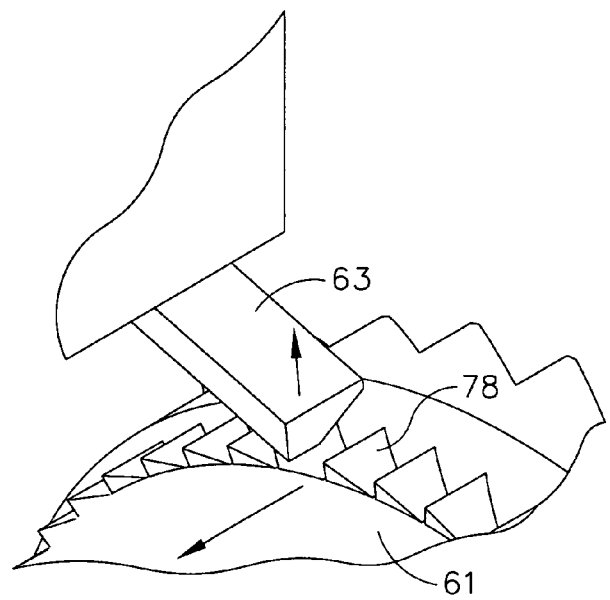
FIG. 9 is a partial perspective view of portions of the ratchet wheel and pawl of the ratchet mechanism of FIG. 7.

Referring to FIGS. 8 and 9, when actuator 58 is brought into close opposition to handle 60 and then released, as described above, pawl 63 can be configured to hold ratchet wheel 61 in position as actuator 58 is returned to its starting position. More particularly, ratchet wheel 61 can include teeth 78 which are configured to permit pawl 63 to slide thereover as actuator 58 is moved toward handle 60 and which are configured to mesh with pawl 63 when actuator 58 is moved in the opposite direction. As a result, ratchet wheel 61 can be rotated by actuator 58 to withdraw sheath 56 without interference from pawl 63, however, pawl 63 can prevent ratchet wheel 61 and sheath 56 from substantially moving as actuator 58 is reset, as described above. Once the position of sheath 56 has been selected, pawl 63 can also hold ratchet wheel 61 in position as surgical instrument 50 is manipulated and operated in the surgical site.

Figure 10:
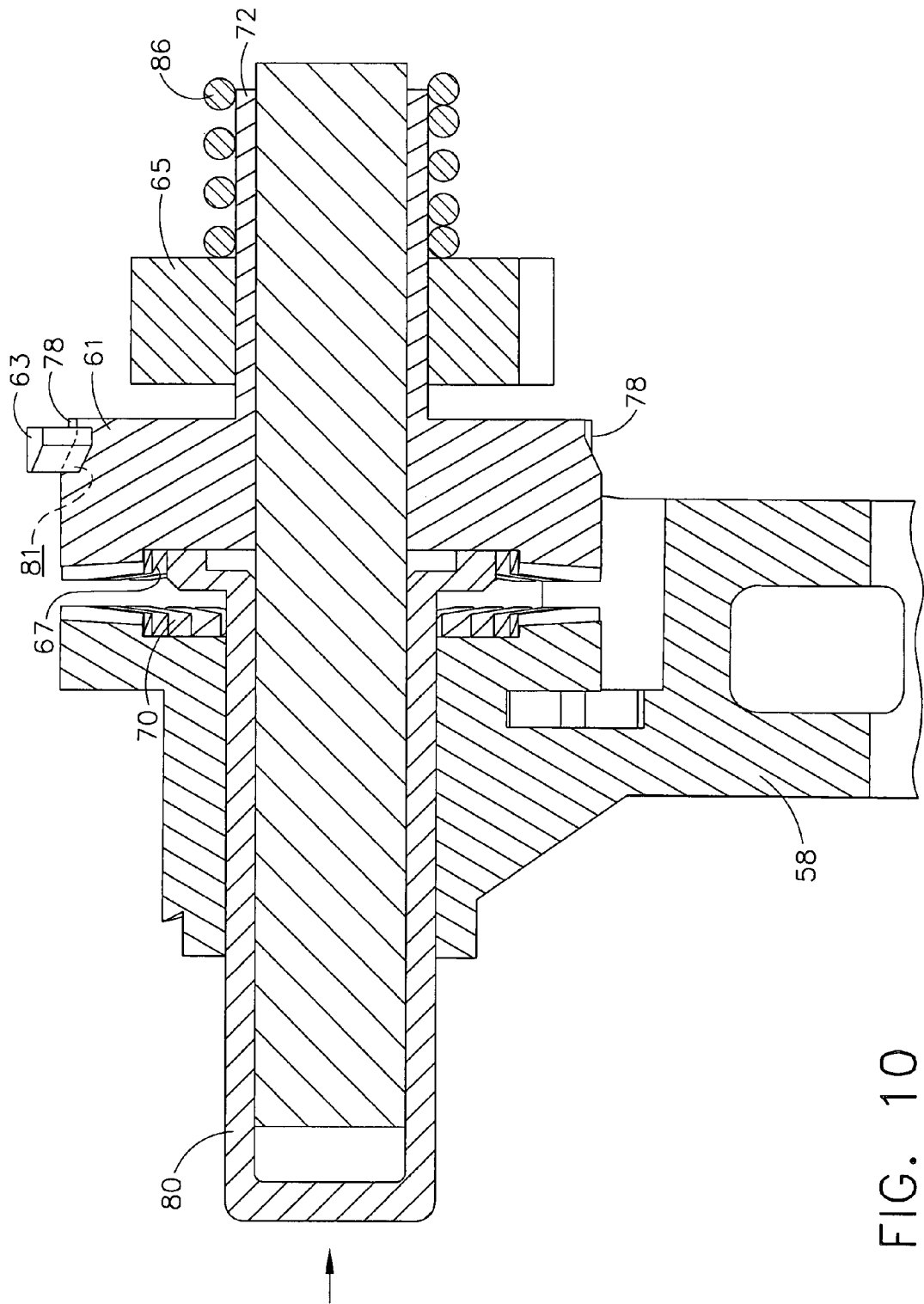
FIG. 10 is a cross-sectional view of the ratchet mechanism of FIG. 7.
Figure 11:
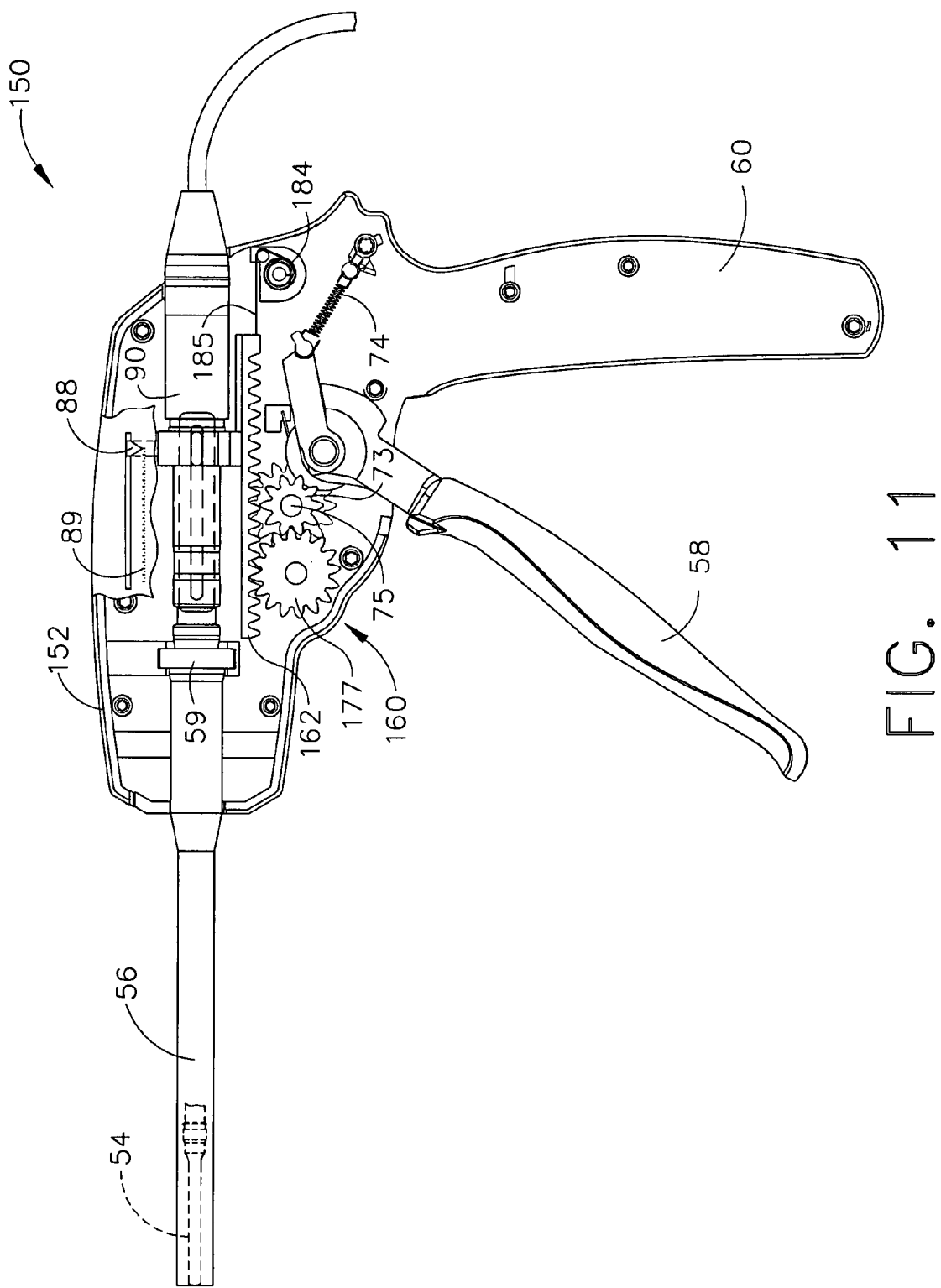
FIG. 11 is a partial cross-sectional view of a surgical instrument in accordance with an alternative embodiment of the present invention.
Figure 12:
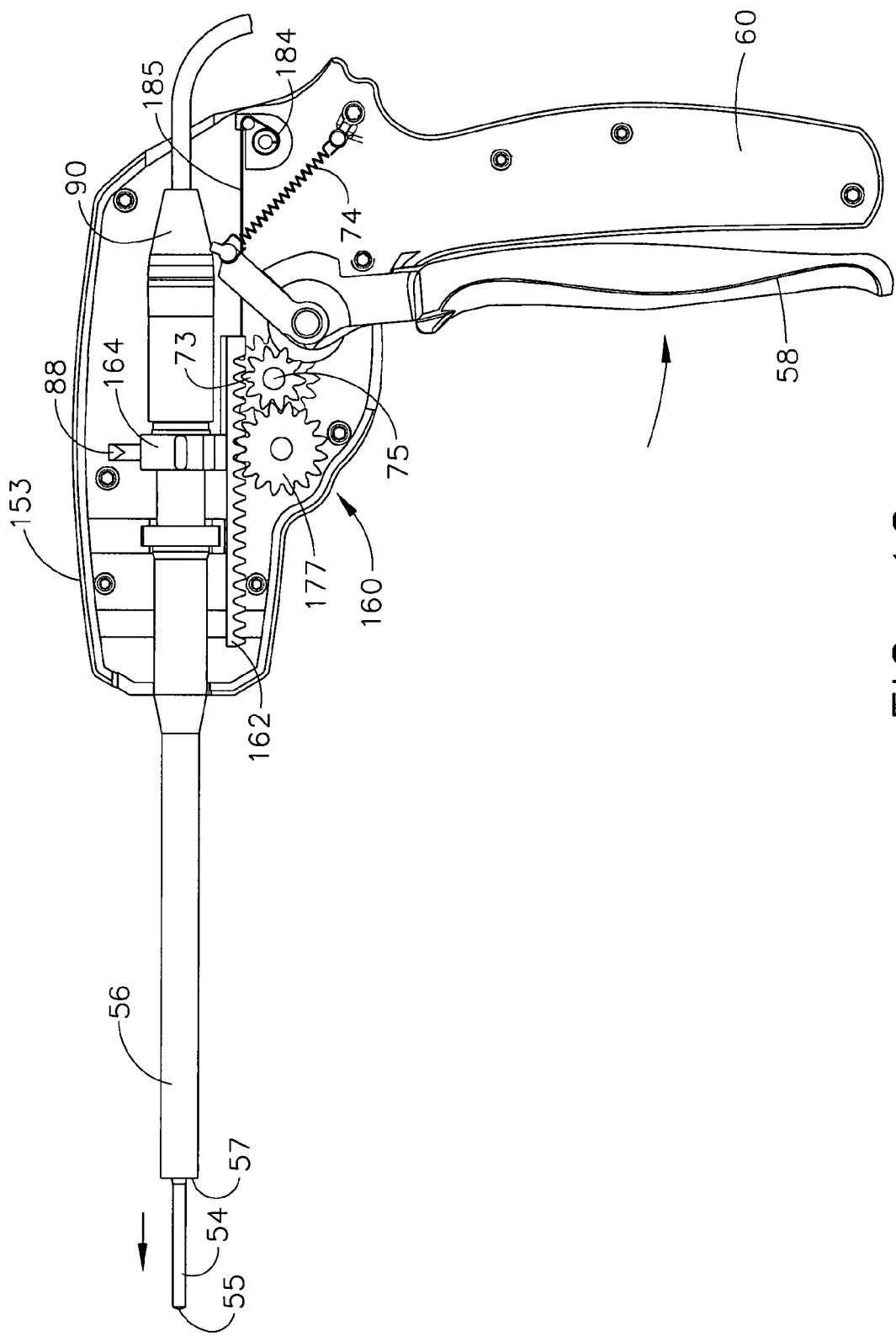
FIG. 12 is a partial cross-sectional view of the surgical instrument of FIG. 11 wherein the end-effector has been extended with respect to the sheath.

To move sheath 56 distally toward distal end 55 of end-effector 54, ratchet mechanism 60 can include a release mechanism which disengages pawl 63 from ratchet wheel 61. More particularly, referring to FIGS. 5-9 and primarily FIG. 10, surgical instrument 50 can further include plunger 80 which extends from actuator 58 and is engaged with ratchet wheel 61 such that when plunger 80 is depressed, ratchet 61 is moved away from pawl 63. Referring to FIG. 10, pawl 63 can include bevel surface 81 which is configured to permit pawl 63 to slide on top of ratchet wheel 61 and allow pawl 63 to be disengaged from teeth 78. Once pawl 63 has been disengaged from teeth 78, sheath 56 can be freely manipulated without interference from ratchet mechanism 60. As a result, the surgeon can move sheath 56 such that it covers distal tip 55 of end-effector 54, or to any other position. In the present embodiment, surgical instrument 50 can include return spring 84 (FIGS. 4-7) which can automatically reposition sheath 56 over distal tip 54 after plunger 80 has been depressed. After sheath 56 has been repositioned, the surgeon may release plunger 80 and allow plunger return spring 86 to reset plunger 80 and, accordingly, allow pawl 63 to reengage ratchet wheel 61.

As described above, a surgeon can use distal end 57 of sheath 56 as a depth stop. In use, the surgeon can select the distance between distal end 57 of sheath 56 and distal end 55 of end-effector 54 such that distance between distal ends 55 and 57 equals the depth to which the surgeon desires to incise the tissue or bone. To assist the surgeon in determining the distance between distal end 55 and distal end 57, surgical instrument 50 can include depth indicator 88. More particularly, referring to FIGS. 3-5, depth indicator 88 can be mounted to rack 62 such that, as rack 62, and, correspondingly, sheath 56, are moved relative to distal end 55 of end-effector 54, depth indicator 88 co-operates with indicia 89 on housing 52 to display the distance between distal tip 57 of sheath 56 and distal tip 55 of end-effector 54. In various embodiments, as a result of manufacturing tolerances, this distance may be approximate; however, care can be taken to reduce impact thereof by controlling and accounting for these tolerances, as known in the art.

Figure 13:
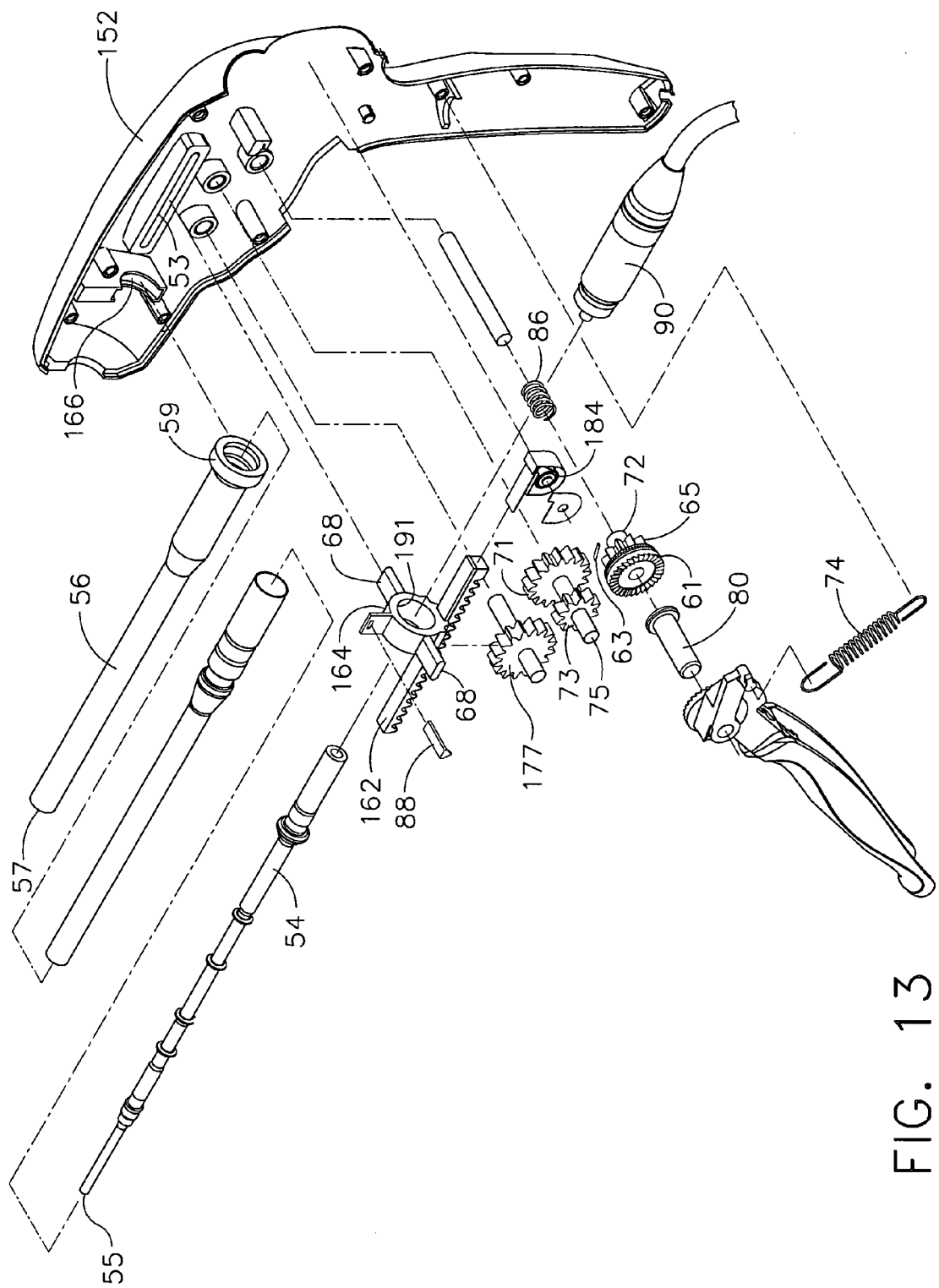
FIG. 13 is an exploded assembly view of the surgical instrument of FIG. 11.
Figure 14:
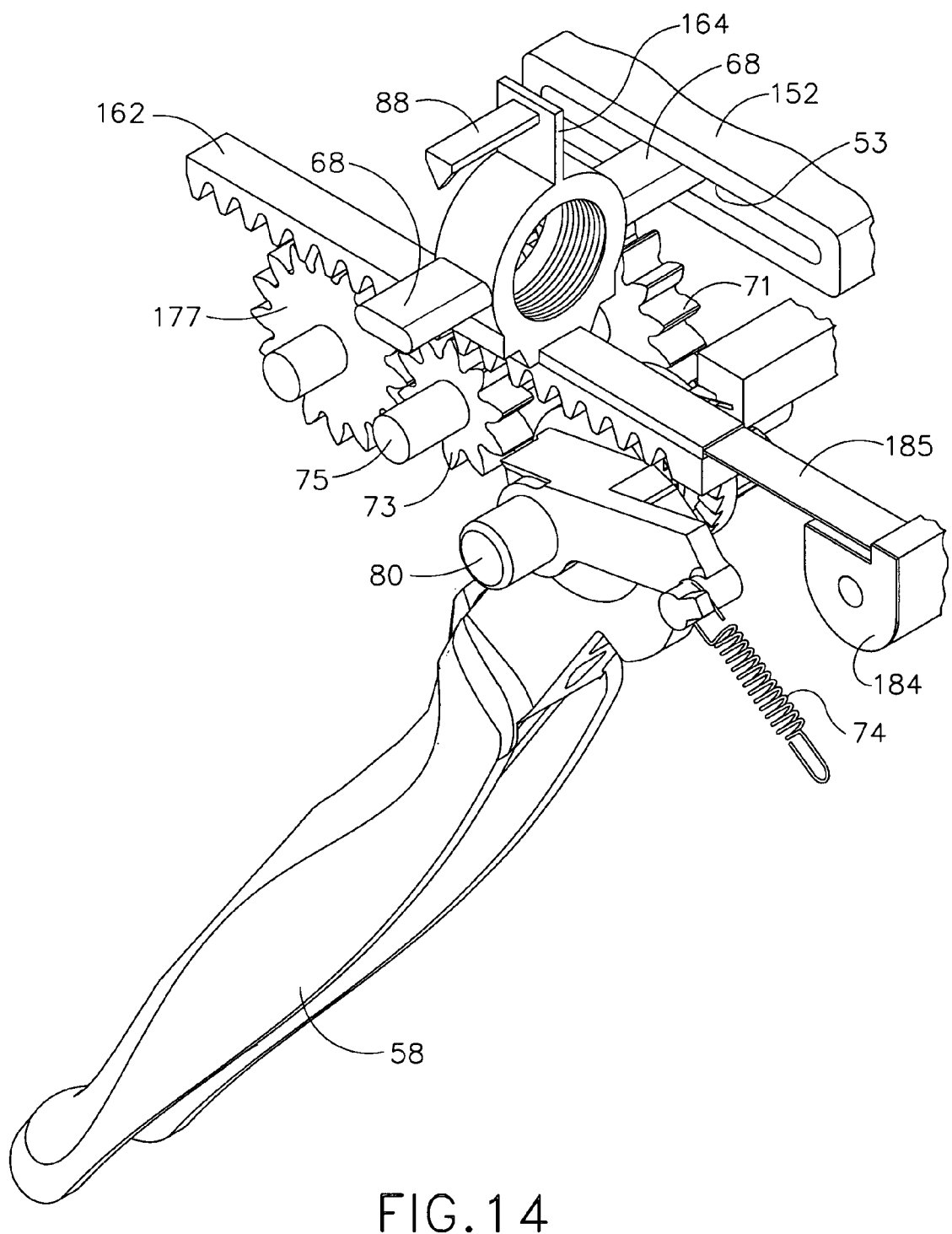
FIG. 14 is a perspective view of the ratchet mechanism of the surgical instrument of FIG. 11.
Figure 15:
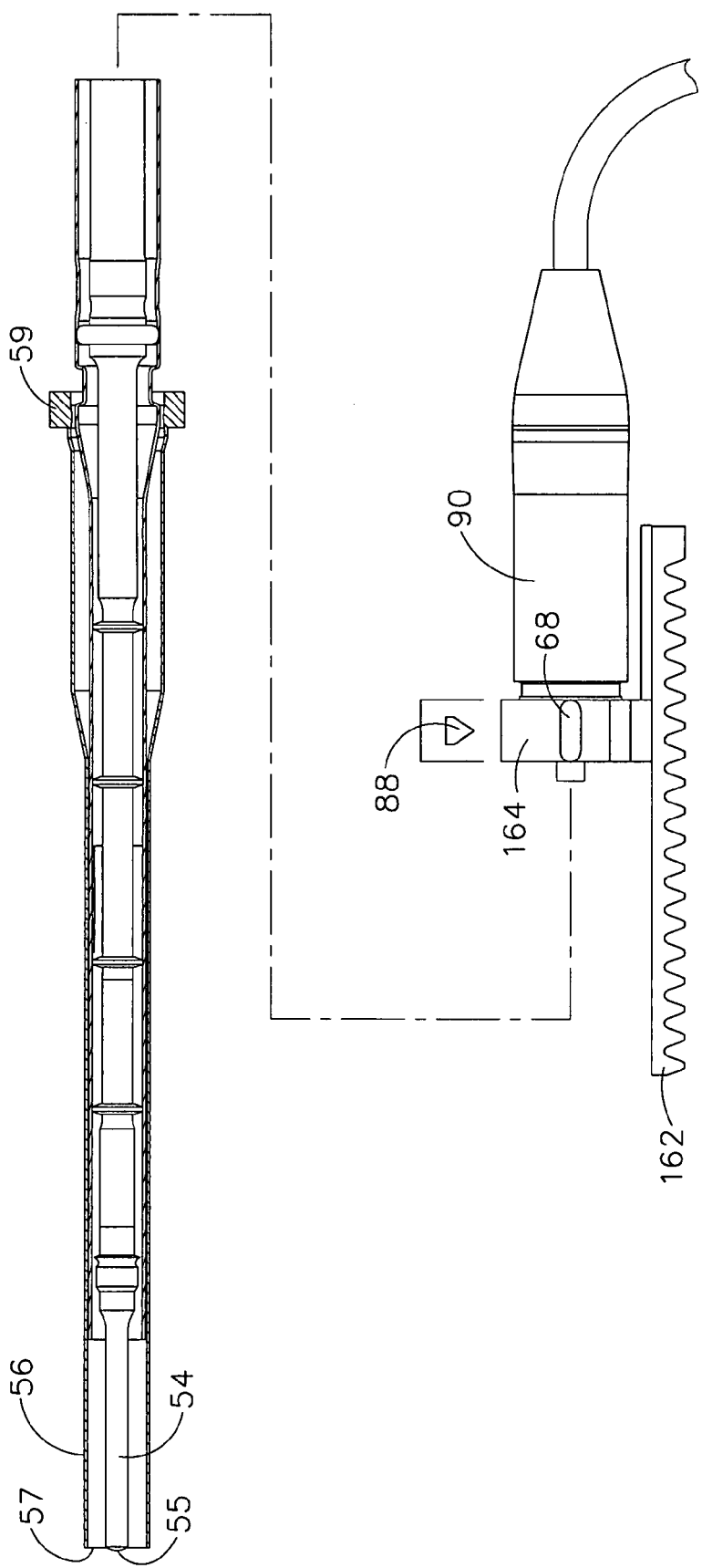
FIG. 15 is a partial exploded assembly view of the sheath, end-effector, and transducer of the surgical instrument of FIG. 11 with some elements shown in cross-section for clarity.
Figure 16:
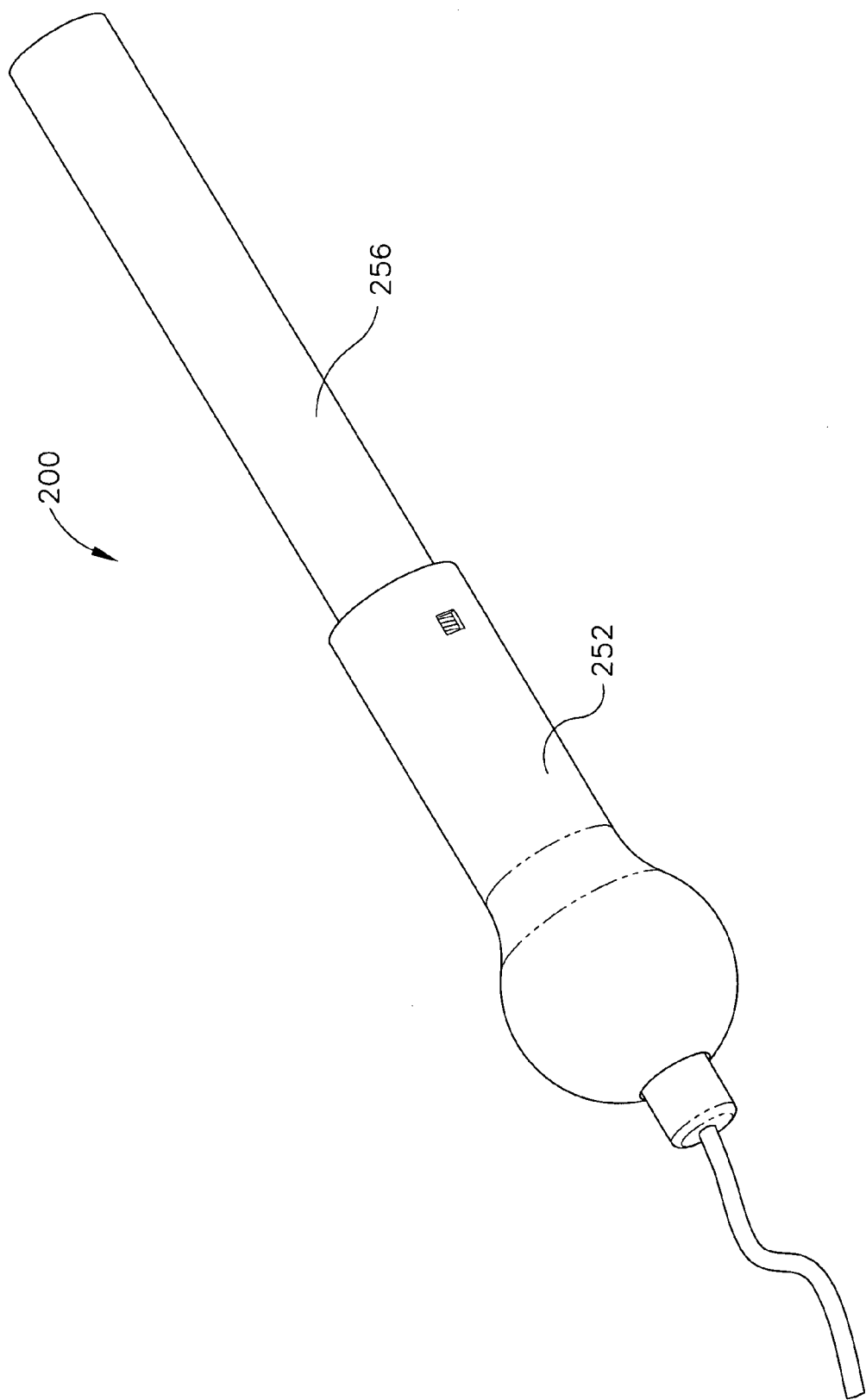
FIG. 16 is a perspective view of a surgical instrument in accordance with an alternative embodiment of the present invention having a handle and a relatively rotatable sheath.
Figure 17:
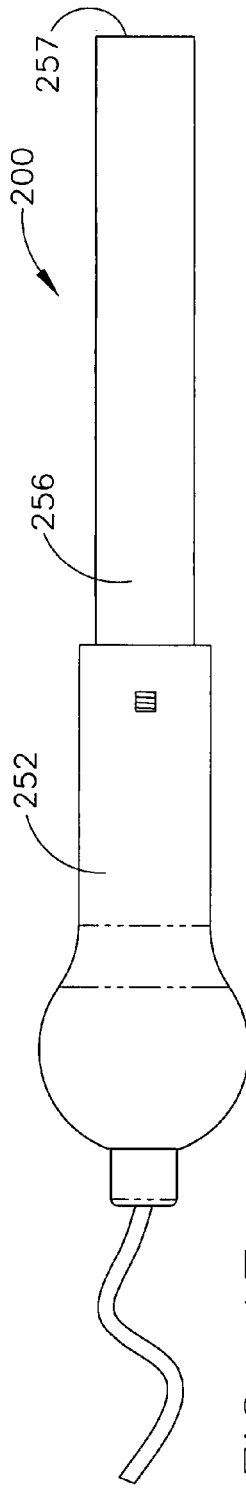
FIG. 17 is a plan view of the surgical instrument of FIG. 16 where the sheath is in a fully extended position.
Figure 19:
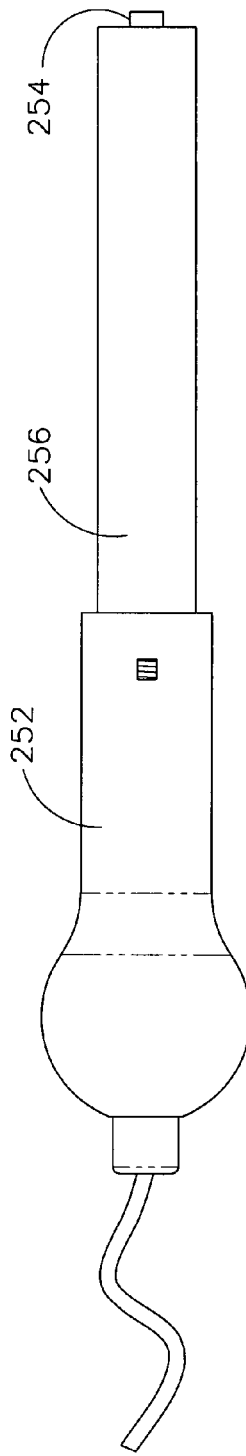
FIG. 19 is a plan view of the surgical instrument of FIG. 16 wherein the sheath is in a partially retracted position.
Figure 20:
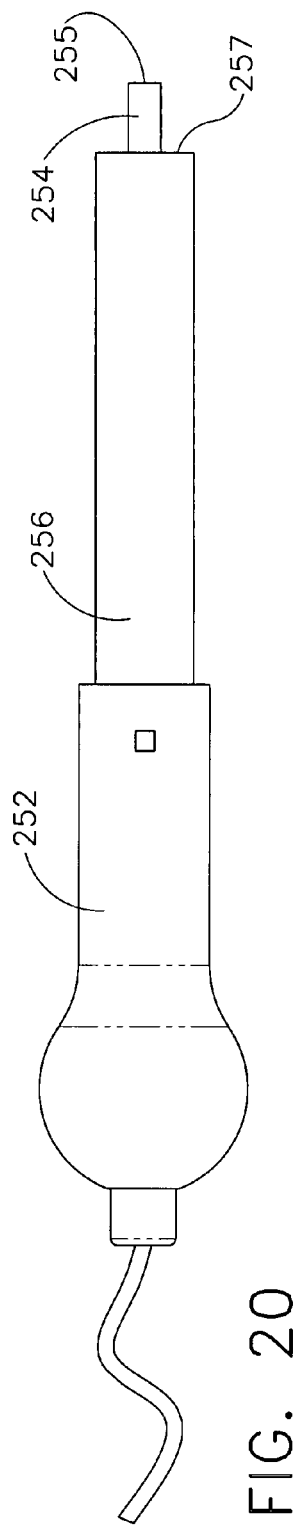
FIG. 20 is a plan view of the surgical instrument of FIG. 16 wherein the sheath is in a retracted position.
Figure 24:
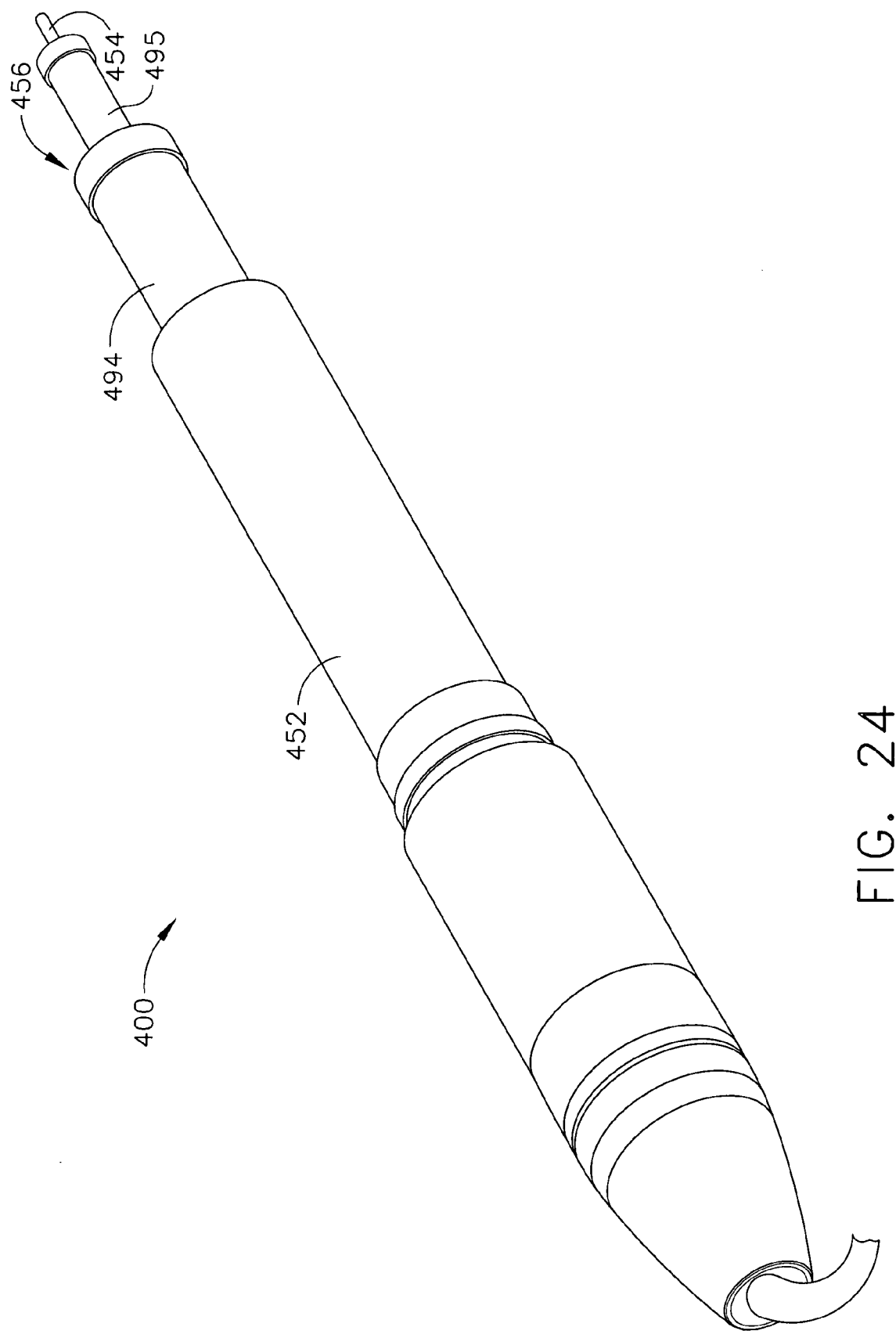
FIG. 24 is a perspective view of a surgical instrument in accordance with an alternative embodiment of the present invention having relatively telescoping portions.
Figure 25:
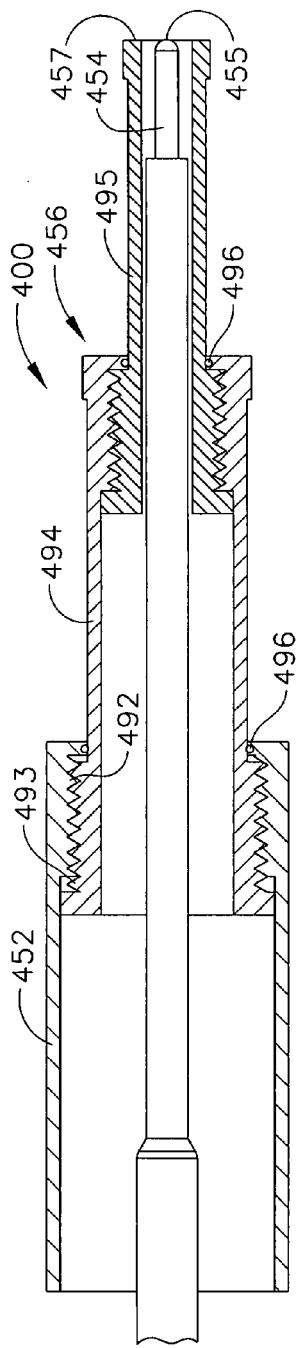
FIG. 25 is a cross-sectional view of the surgical instrument of FIG. 24 in a fully extended configuration.
Figure 26:
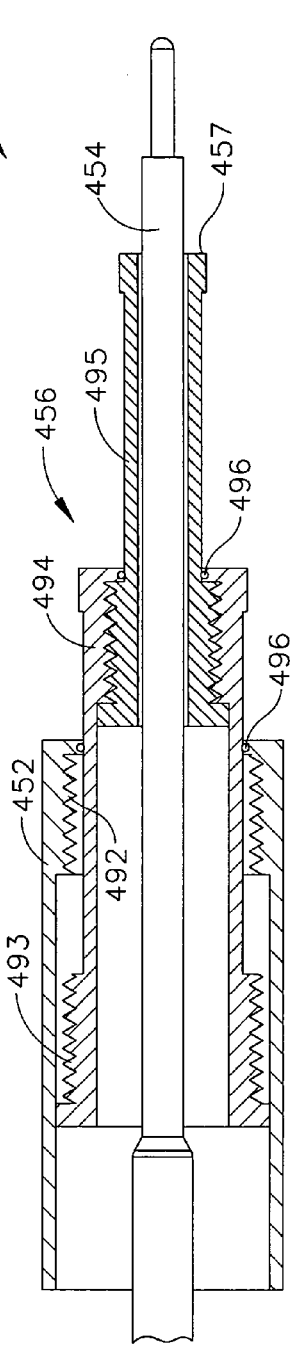
FIG. 26 is a cross-sectional view of the surgical instrument of FIG. 24 in a partially retracted configuration.
Figure 27:
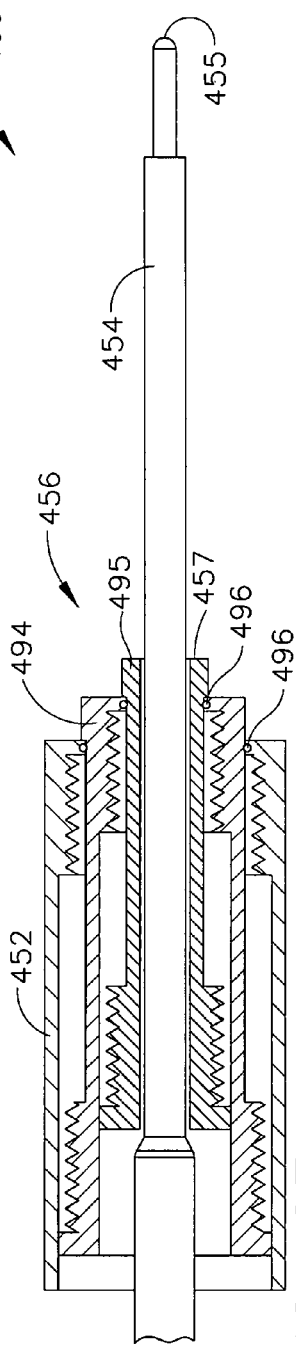
FIG. 27 is a cross-sectional view of the surgical instrument of FIG. 24 in a fully retracted configuration.

In the present embodiment, transducer 90 can be mounted to housing 52 as known in the art. In alternative embodiments, referring to surgical instrument 150 illustrated in FIGS. 11-15, transducer 90 can be mounted to rack 162 such that transducer 90 can be moved relative to housing 152. In these embodiments, the distance between distal tip 55 of end-effector 54 and distal tip 57 of sheath 56 can be adjusted by moving end-effector 54 and transducer 90 relative to sheath 56. In such embodiments, referring to FIG. 13, sheath 56 can be mounted to housing 152 via flange 59 and slot 166 and transducer 90 can be mounted within aperture 191 of collar 164. Surgical instrument 150 can also include ratchet mechanism 160 for moving end-effector 54 relative to distal end 57 or sheath 56. Notably, referring primarily to FIG. 14, the gear train of ratchet mechanism 160 includes one gear more than ratchet mechanism 60, i.e., gear 177, and, as a result, operation of actuator 58 causes rack 162 to advance distally instead of withdrawing proximally as described in the embodiments above. Furthermore, surgical instrument 150 can include return spring 184 which is configured retract rack 162 and end-effector 54. Return spring 184, in the present embodiment, includes a flexible band 185 which is attached to rack 162 and is elastically biased such that return spring 184 is configured to retract and coil flexible band 185 therein.

In various embodiments of the present invention, a surgical instrument can include a sheath which is rotatably extendable and/or retractable with respect to the housing of the surgical instrument. Referring to FIGS. 16-21, surgical instrument 200 can include housing 252, end-effector 254, and sheath 256. Housing 252 and sheath 256 can include threads 292 and 293, respectively, which are threadably engaged such that one of housing 252 and sheath 256 can be rotated with respect to the other to extend or retract distal end 257 of sheath 256 with respect to distal end 255 of end-effector 254. In various embodiments, threads 292 and 293 may be comprised of fine-pitch threads which hold the relative position of housing 252 and sheath 256 in a substantially fixed position. However, in various other embodiments, although not illustrated, surgical instrument 200 may include features for more positively securing the relative position of housing 252 and sheath 256. In at least one such embodiment, surgical instrument 200 can include a collar which is threaded over at least a portion of housing 252 and sheath 256 to fixedly retain them in position.

In various embodiments, the surgical instrument can include, referring to FIGS. 22 and 23, indicia 389 and depth gauge 388 which, similar to the above, can be used by a surgeon to evaluate the distance between distal end 357 of sheath 356 and distal end 355 of end-effector 354. More particularly, in the present embodiment, the distal edge of housing 352, i.e., depth gauge 388, can be used by the surgeon as a datum by which indicia 389 are evaluated. As described above, once the distance between distal ends 355 and 357 has been set, end-effector 354 can be inserted into the tissue of bone, for example, until distal end 357 of sheath 356 contacts the tissue or bone. In various embodiments, distal end 357 can comprise a flared, or bell-shaped, end which can be configured to push tissue surrounding the surgical site, for example, away from end-effector 354 to prevent accidental injury thereto.

In various embodiments of the present invention, a surgical instrument can include a sheath comprising two or more telescoping portions. Referring to FIGS. 24-27, surgical instrument 400 can include housing 452, end-effector 454, and sheath 456. In at least one embodiment, housing 452 can comprise an outer portion and sheath 456 can include intermediate portion 494 and inner portion 495. Similar to the above, intermediate portion 494 can be threadably engaged with and rotated relative to housing 452 and inner portion 495 can be threadably engaged with and rotated relative to intermediate portion 494 in order to extend and/or retract distal end 457 of sheath 456 with respect to distal end 455 of end-effector 454. In various embodiments, intermediate portion 494 and inner portion 495 can include distal and/or proximal stops which can limit the relative movement therebetween. In at least one embodiment, surgical instrument 400 can include seals 496, such as rubber O-rings, for example, which seal gaps between housing 452, intermediate portion 494 and outer portion 495.

Figure 28:
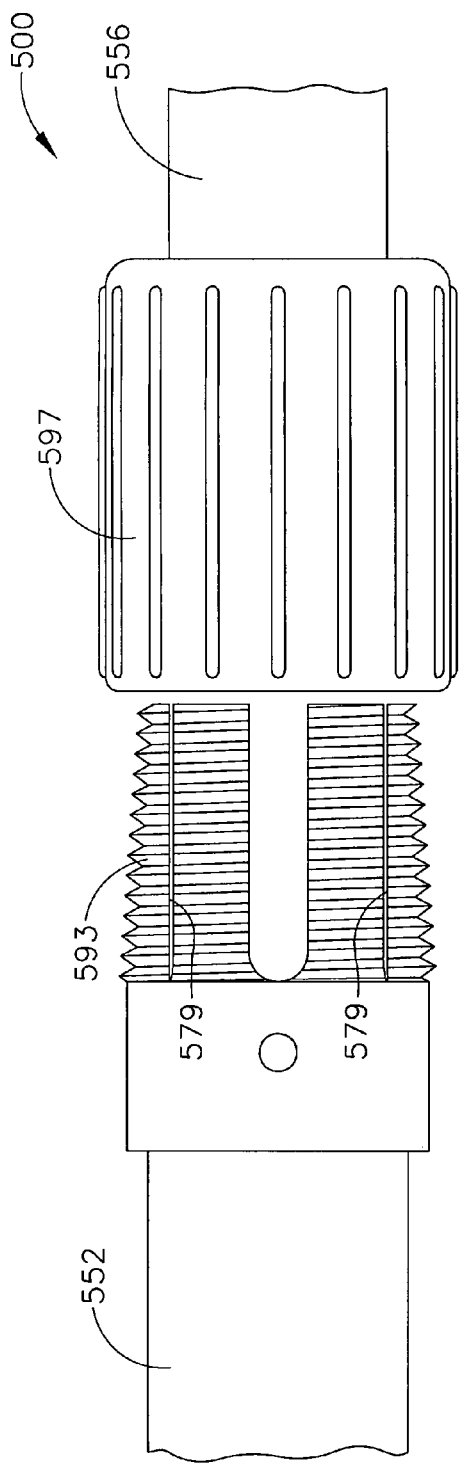
FIG. 28 is a partial plan view of a surgical instrument in accordance with an alternative embodiment of the present invention.
Figure 29:
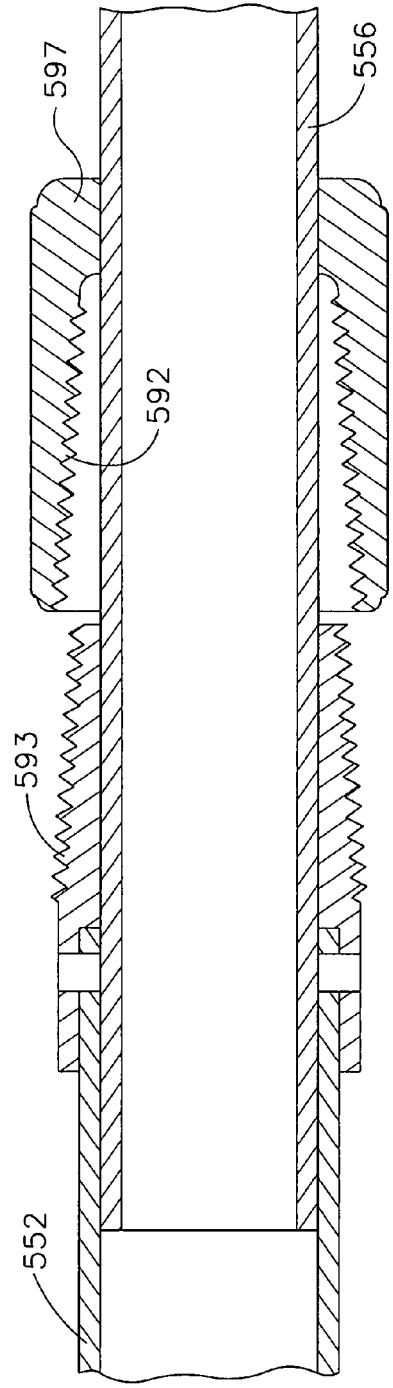
FIG. 29 is a cross-sectional view of the surgical instrument of FIG. 28.

In various embodiments of the present invention, a surgical instrument can include at least two relatively collet-like slidable portions and a collar, for example, for fixedly securing the slidable portions together. More particularly, referring to FIGS. 28 and 29, surgical instrument 500 can include housing 552, sheath 556, and collar 597. In use, a surgeon can slide sheath 556 within housing 552 to position, similar to the above, the distal end of sheath 556 with respect to the distal end of the end-effector. Thereafter, the surgeon may thread collar 597 onto the threaded end of housing 552 to compress housing 552 against the outside surface of sheath 556 positioned therein. As a result of this compression, the relative position of housing 552 and sheath 556 can be substantially fixed and prevented from sliding relative to each other. In at least one embodiment, referring to FIG. 28, the threaded end of housing 552 can include slits 579 which divide the threaded end of housing 552 into independently deflectable portions which can be more easily displaced by collar 597. In various other embodiments, although not illustrated, housing 552 can be configured to slide within sheath 556 and collar 597 can be configured to compress sheath 556 against housing 552.

Figure 30:
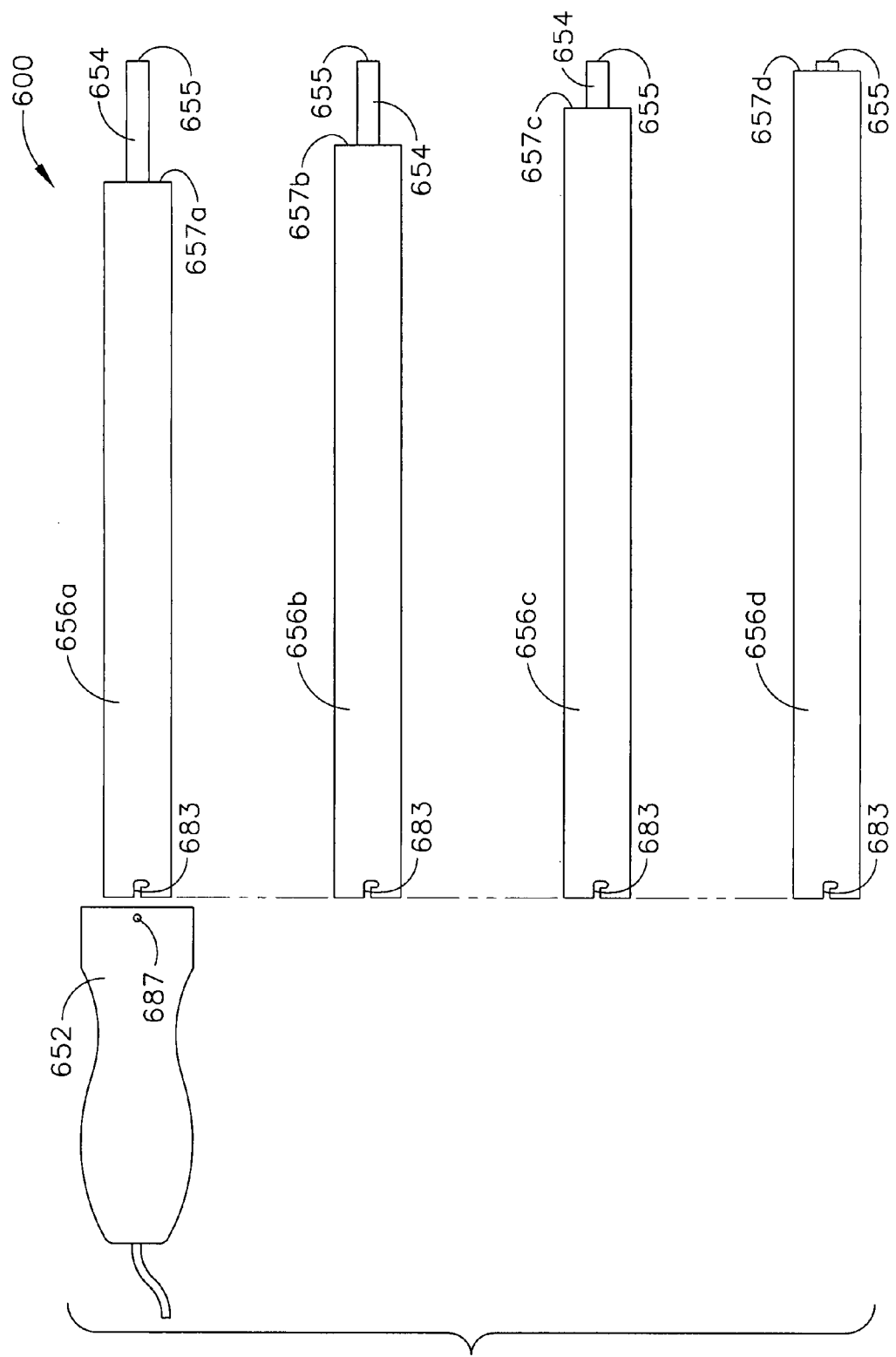
FIG. 30 is a schematic of a surgical kit including a surgical instrument and a plurality of removably attachable sheaths in accordance with an alternative embodiment of the present invention.

In various embodiments of the present invention, a surgical instrument can include a detachable sheath. More particularly, in at least one embodiment, referring to FIG. 30, a kit can be provided to a surgeon containing surgical instrument 600 having housing 652 and end-effector 654, and a plurality of sheaths having different lengths and/or configurations, for example. In the illustrated embodiments, the kit can include sheaths 656a, 656b, 656c and 656d, wherein each sheath has a different length. In use, a surgeon can select a sheath 656 from the kit that provides a desired distance between distal tip 655 of end-effector 654 and the distal tip 657 of the selected sheath 656. As a result, the surgeon can control the depth to which end-effector 654 is inserted into tissue or bone, for example, by selecting the appropriate sleeve 656. To facilitate the attachment of the selected sheath 656 to housing 652, each sheath 656 can include at least one slot 683 which can be sized and configured to receive a projection 687 extending from housing 652 and retain the sheath thereto. In various embodiments, each slot 683 can be configured to receive a projection 687 in press-fit engagement, for example, to assure a secure fit therebetween. In the illustrated embodiments, slots 683 are L-shaped such that the sheath 656 can be 'twist-locked' onto housing 652. Although not illustrated, the sheaths can include projections extending therefrom and housing 652 can include slots configured to receive the projections, or any combination thereof. Furthermore, although not illustrated, the sheath can be comprised of several portions. In at least one such embodiment, the sheath can comprise an adapter attached to the housing where the adapter is configured to removably receive one of several different end-portions. In various embodiments, the sheath can include several portions which are selectively joined together to adjust the overall length of the sheath.

Figure 31:
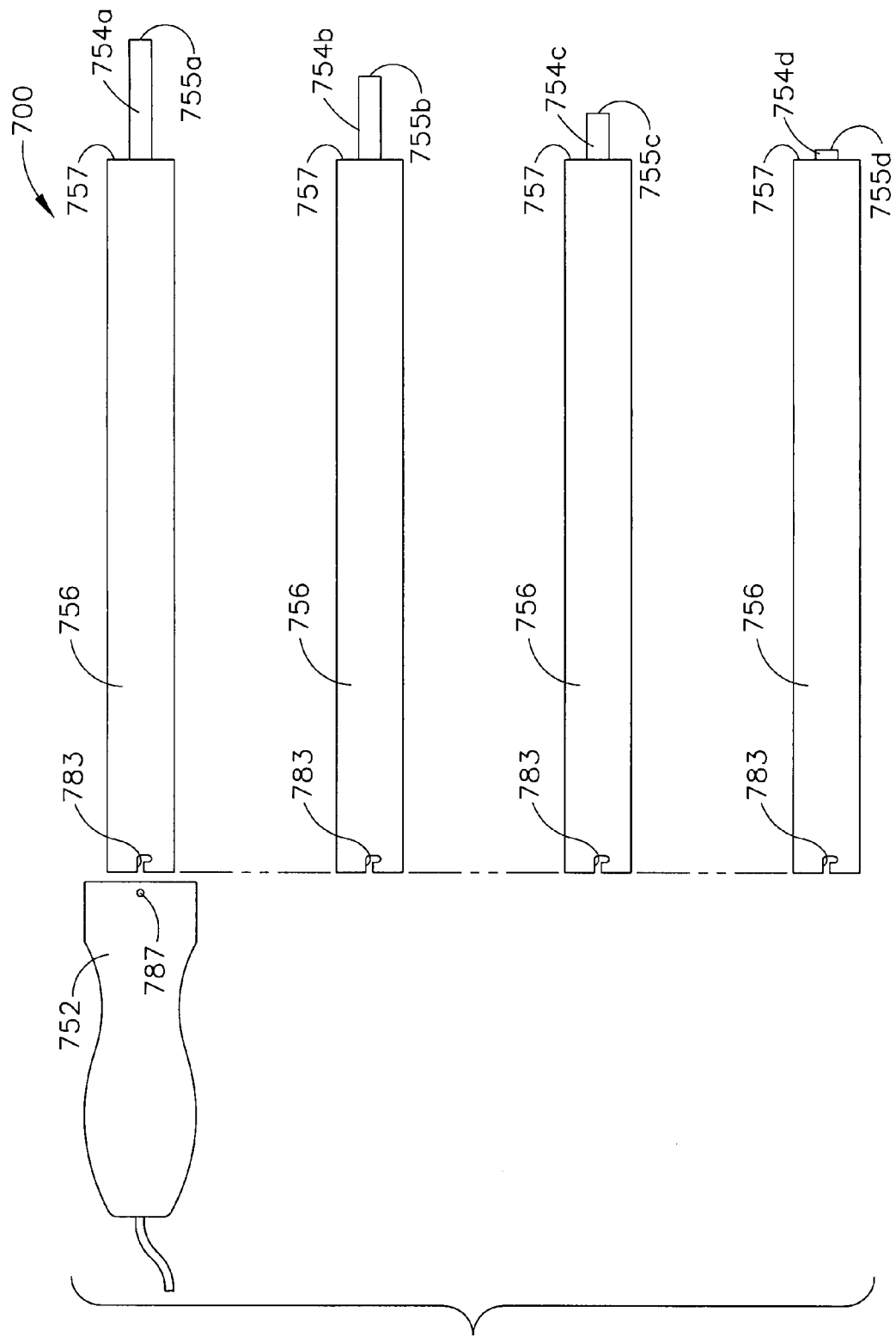
FIG. 31 is a schematic of a surgical kit including a surgical instrument and a plurality of removably attachable end-effectors in accordance with an alternative embodiment of the present invention.
Figure 32:
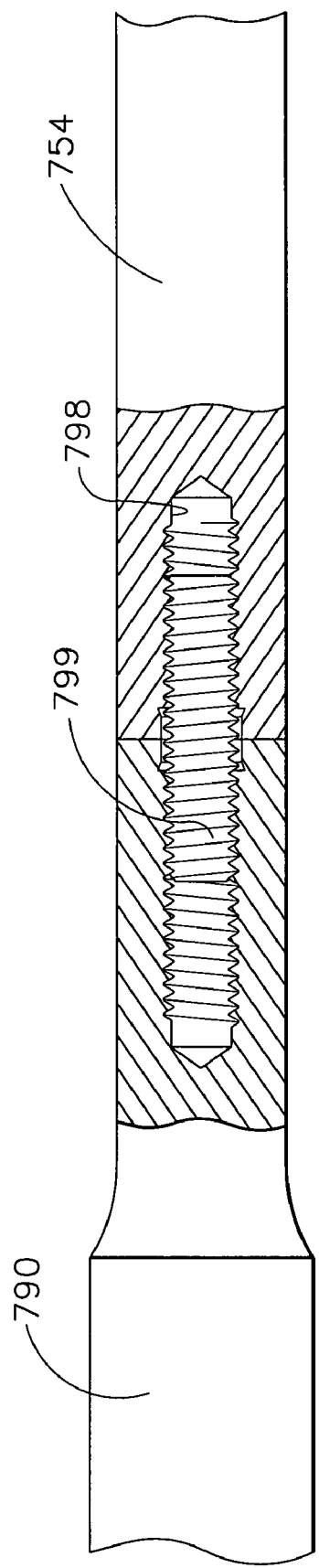
FIG. 32 is a partial cross-sectional view of the interconnection between an end-effector and the transducer of the surgical instrument of FIG. 31.

In various embodiments of the present invention, a surgical instrument can include a detachable end-effector. More particularly, in at least one embodiment, referring to FIG. 31, a kit can be provided to a surgeon containing surgical instrument 700 having housing 752 and sheath 756, and a plurality of end-effectors having different lengths and/or configurations, for example. In the illustrated embodiment, the kit can include end-effectors 754a, 754b, 754c and 754d, wherein each end-effector has a different length. In use, a surgeon can select an end-effector 754 from the kit that provides a desired distance between distal tip 757 of sheath 756 and the distal tip 755 of the selected end-effector 754. As a result, the surgeon can control the depth to which end-effector 754 is inserted into tissue or bone, for example, by selecting the appropriate end-effector 754. To facilitate the attachment of the selected end-effector 754 to transducer 790, referring to FIG. 32, each end-effector 754 can include a threaded recess 798 which is configured to receive a threaded portion of transducer 790 or a threaded fastener 799 extending therefrom.

Figure 33:
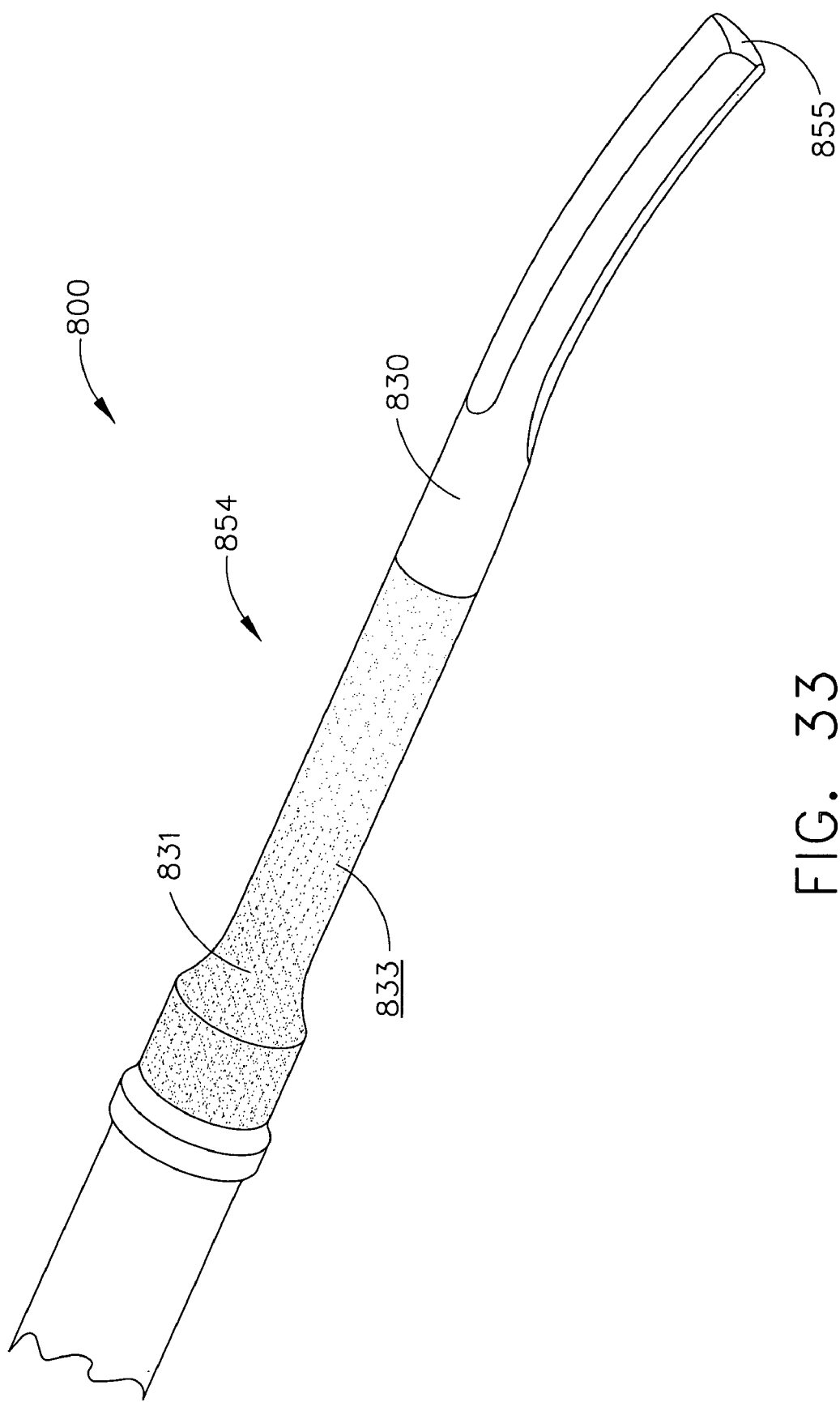
FIG. 33 is a partial perspective view of a surgical instrument in accordance with an alternative embodiment of the present invention having a first treatment region and a second treatment region.
Figure 34:
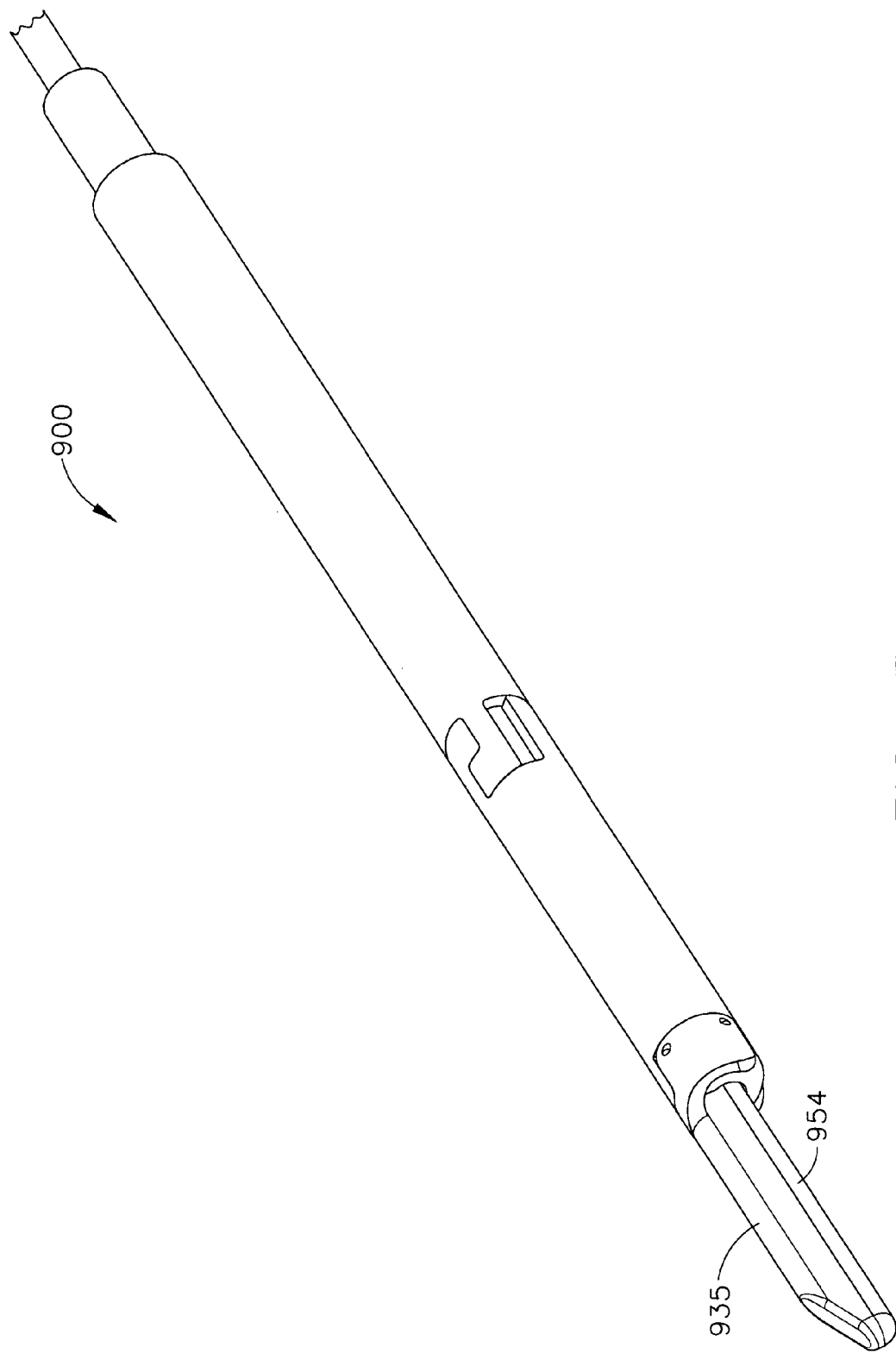
FIG. 34 is a partial perspective view of a surgical instrument in accordance with an alternative embodiment of the present invention including a retractable clamp.

In various embodiments of the present invention, a surgical instrument can include an end-effector having at least one indicium or demarcation which is configured to identify a treatment region of the end-effector. More particularly, the end-effector can, referring to FIG. 33, include first and second treatment regions, for example, which can be used by a surgeon to treat tissue, for example. In at least one such embodiment, end-effector 854 can include first treatment region 830 and second treatment region 831, where first treatment region 830 includes a cutting edge for incising tissue, for example, and second treatment region 831 includes an arcuate surface for cauterizing or coagulating tissue, for example. Referring to FIG. 33, surface 833 of second treatment region 831 can include an indicium or demarcation that allows a surgeon to more easily identify second treatment region 831 and, by negative implication, first treatment region 830. In alternative embodiments, first treatment region 830 may include at least one indicium or demarcation that is different than the indicium or demarcation identifying second treatment region 831.

In various embodiments, the indicium may include a coated surface. Such coating can be applied by conventional methods including annodization, for example. In embodiments where both first treatment region 830 and second treatment region 831 are coated, the coatings can have different colors, textures, thicknesses and/or be comprised of different materials, for example. In various embodiments, one of the treatment regions may be dyed such that it has a different color than the other treatment region. In at least one embodiment, a treatment region having a cutting edge or surface may be coated or dyed with a material having a bright color, such as red, orange or yellow, for example. Similarly, a treatment region having a surface for cauterizing or coagulating tissue may be coated or dyed with a material having a dark color such as green, blue or indigo, for example. In various embodiments, at least one of the surfaces of first treatment region 830 and second treatment region 831 can have a modified surface finish. In at least one such embodiment, at least a portion of the surface can be etched or bead-blasted, for example, to create a textured surface finish. In embodiments where both treatment regions are etched, for example, the degree of etching may be different to allow the surgeon to more readily distinguish between the treatment regions. In at least one embodiment, the indicium can include numbers, letters or symbols printed thereon or engraved therein.

In various embodiments, the demarcation may include at least one groove in the surface of the end-effector which can provide delineation between the treatment regions. In at least one embodiment, the entire surface of a treatment region can include a plurality of grooves that may, in various embodiments, be arranged in an organized pattern of hatching, for example. In at least one embodiment, the first and second treatment regions can both include grooves or other demarcations where the density of the grooves or demarcations can be different in the first treatment region than in the second treatment region. In various embodiments, the density of the demarcations can include gradual changes which can be configured indicate changes in the intensity or amplitude of vibrations, for example, along the length of the end-effector. As a result of such changes in the demarcations, a surgeon can readily discern portions of the end-effector vibrating at maximum and minimum intensities and intensities therebetween. In at least one such embodiment, the density of pigmentation, for example, on an end-effector can be greatest at a node, or anti-node, for example, and gradually decrease at increasing distances from the node, or anti-node. In various embodiments, the rate of change in the density of pigmentation, for example, can be linear or, in other embodiments, it can be geometric. Embodiments having a geometric rate of change in the demarcations can, in at least some embodiments, more accurately represent the change in the intensity of the vibrations caused by the standing sinusoidal wave. Although the embodiments outlined above have been described as having first and second treatment regions, the present invention is not so limited. On the contrary, the end-effector may include more than two treatment regions each having at least one indicium and/or demarcation or no indicium or demarcation at all.

Further to the above, in various embodiments, at least one indicium or demarcation can be used to identify portions of the end-effector which have either high or low vibrational intensities or amplitudes, for example. More particularly, as described above, the transducer of the surgical instrument can generate a standing wave in the end-effector which creates nodes and anti-nodes along the length of the end-effector. These nodes and anti-nodes represent high and low regions of vibrational intensity, respectively, of the end-effector which can be utilized by a surgeon. For example, the high intensity regions of the end-effector can be used to incise or cauterize tissue, for example, whereas the low intensity regions of the end-effector can be used to safely contact the tissue surrounding the surgical site. As these nodes and anti-nodes are typically indiscernible to the surgeon, an indicium or demarcation may be provided on the end-effector to allow the surgeon to readily discern these regions of the end-effector.

In various embodiments of the present invention, a surgical instrument can include a retractable clamp configured to hold at least a portion of a bone or tissue, for example, against the end-effector of the surgical instrument. In at least one embodiment, the clamp, when it is extended, can be configured to act as a rongeur or kerrison, for example, configured to hold at least a portion of a bone against the end-effector to remove small portions of the bone. The clamp, when it is at least partially retracted, can allow the end-effector to be used as an ultrasonic cobb or curette to dissect tissue or elevate the tissue from a bone, for example. In addition, the end effector can, when the clamp is at least partially retracted, be used as an osteotome and can be used to chisel or resect bone without the use of ultrasonic energy.

Figure 35:
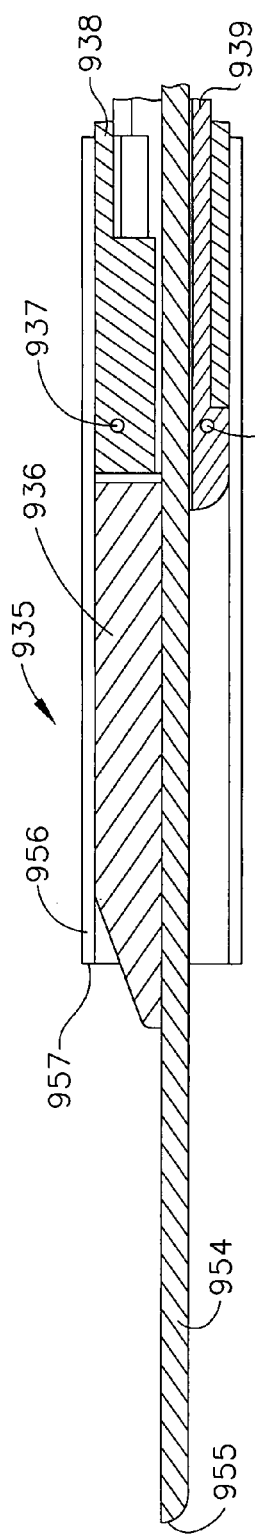
FIG. 35 is a partial cross-sectional view of the surgical instrument of FIG. 34 where the clamp is in a retracted position.
Figure 36:
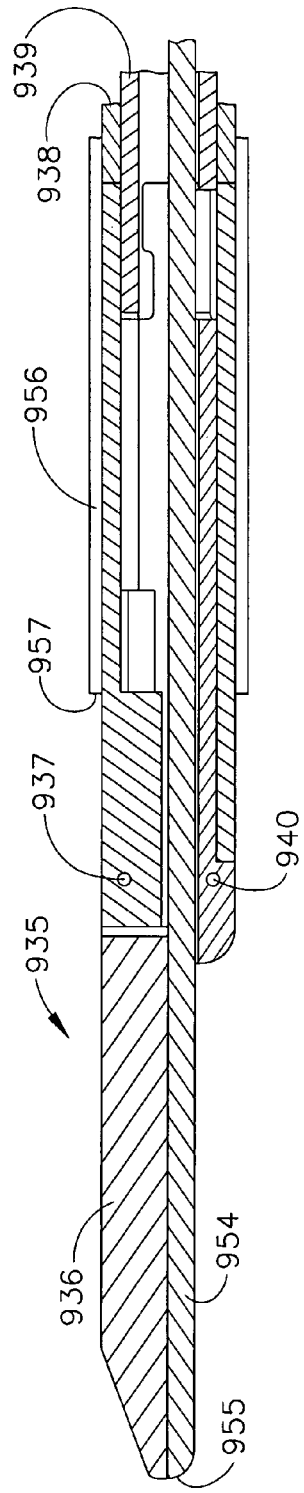
FIG. 36 is a partial cross-sectional view of the surgical instrument of FIG. 34 where the clamp is in an extended position.
Figure 37:
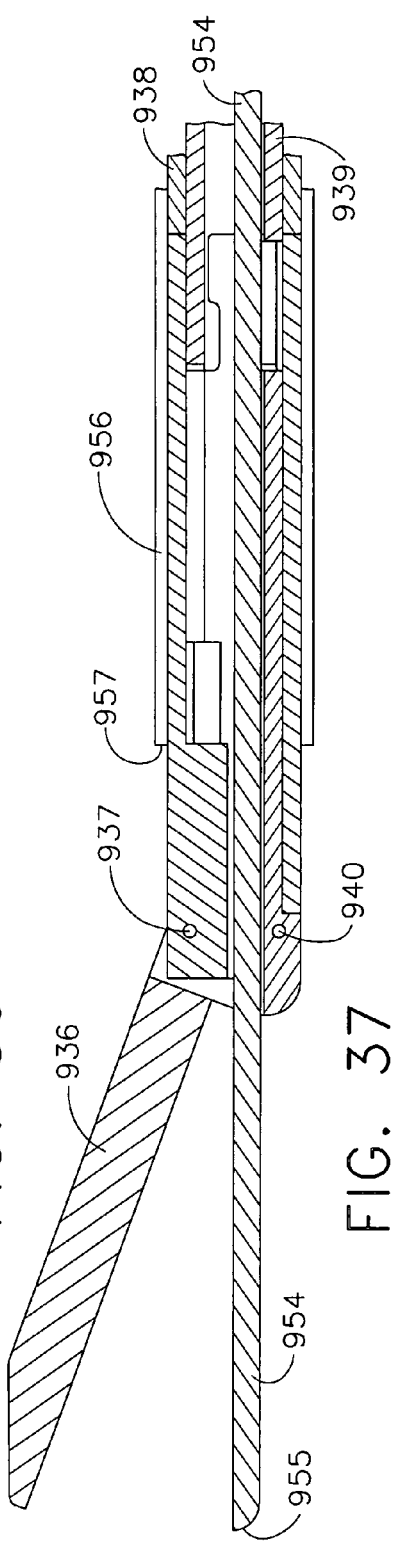
FIG. 37 is a partial cross-sectional view of the surgical instrument of FIG. 34 where the jaw member of the clamp has been moved into an open position.

In various embodiments, referring generally to FIGS. 34-44, surgical instrument 900 can include end-effector 954 and retractable clamp 935. Referring primarily to FIGS. 35-37, retractable clamp 935 can include jaw member 936 and pivot 937 where pivot 937 provides an axis about which jaw member 936 can be rotated. Retractable clamp 935 can be connected to inner member 938 which can, as described in greater detail below, be operably engaged with a first actuator. In use, the first actuator can be configured to move clamp 935 between its retracted position illustrated in FIG. 35 and its extended position in FIG. 36. Once extended, jaw member 936 can be rotated about pivot 937, as illustrated in FIG. 37, so that jaw member 936 can be placed on one side of a bone or tissue and end-effector 954 can be placed on the opposite side of the bone or tissue. Jaw member 936 can then be closed onto the bone or tissue and the ultrasonic energy transmitted to end-effector 954 from the transducer can be used to cut or seal the bone or tissue therebetween. As discussed in greater detail below, jaw member 936 can also be engaged with outer member 939 via drive pin 940 where outer member 939 and drive pin 940 can be configured to rotate jaw member 936 about pivot 937.

In various embodiments, referring to FIG. 39, surgical instrument 900 can further include first actuator 941. As indicated above, first actuator 941 can be operably engaged with outer member 938 and can be configured to extend or retract clamp 935. More particularly, referring to FIG. 39, first actuator 941 can include plungers 942 which can be biased into engagement with housing 952 by springs 943 in order to hold outer member 938 in one of several predetermined positions. For example, when plungers 942 are engaged and retained with recesses 944 in housing 952, clamp 935 can be in its extended position as illustrated in FIG. 35. In order to move clamp 935 into at least a partially extended position, plungers 942 can be depressed to disengage them from recesses 944 and allow outer member 938, and clamp 935, to be moved distally. Similar to the above, clamp 935 can be held and retained in position, including its fully extend position illustrated in FIG. 35, when plungers 942 are engaged with other recesses of housing 952. Although only a few sets of recesses are illustrated in FIG. 39, several sets of recesses or other retention features, referring to FIG. 38, can be used to retain outer member 938, and clamp 935, in position. In order to retract outer member 938 and clamp 935, plungers 942 can be depressed and moved proximally.

In various embodiments, referring to FIGS. 40 and 41, surgical instrument 900 can further include second actuator 945. Second actuator 945 can be operably engaged with inner member 937 and can be configured to move, or rotate, jaw member 936 about pivot 937 as described above. More particularly, second actuator 945 can include lever 946 and linkage 947 which operably connects lever 946 and inner member 939. In use, referring to FIG. 41, lever 946 can be moved from an open position, i.e., its position illustrated in dashed lines in FIG. 41, and a closed position, i.e., its position illustrated in solid lines. In its open position, lever 946 and linkage 947 are configured to retain jaw member 936 in its open position, i.e., its position illustrated in FIG. 37. As lever 946 is moved into is closed position, linkage 947 is configured to retract inner member 939 and close jaw member 936, i.e., bring it into close opposition to distal end 955 of end-effector 954. To reopen jaw member 936, lever 946 is moved into its open position described above.

Figure 42:
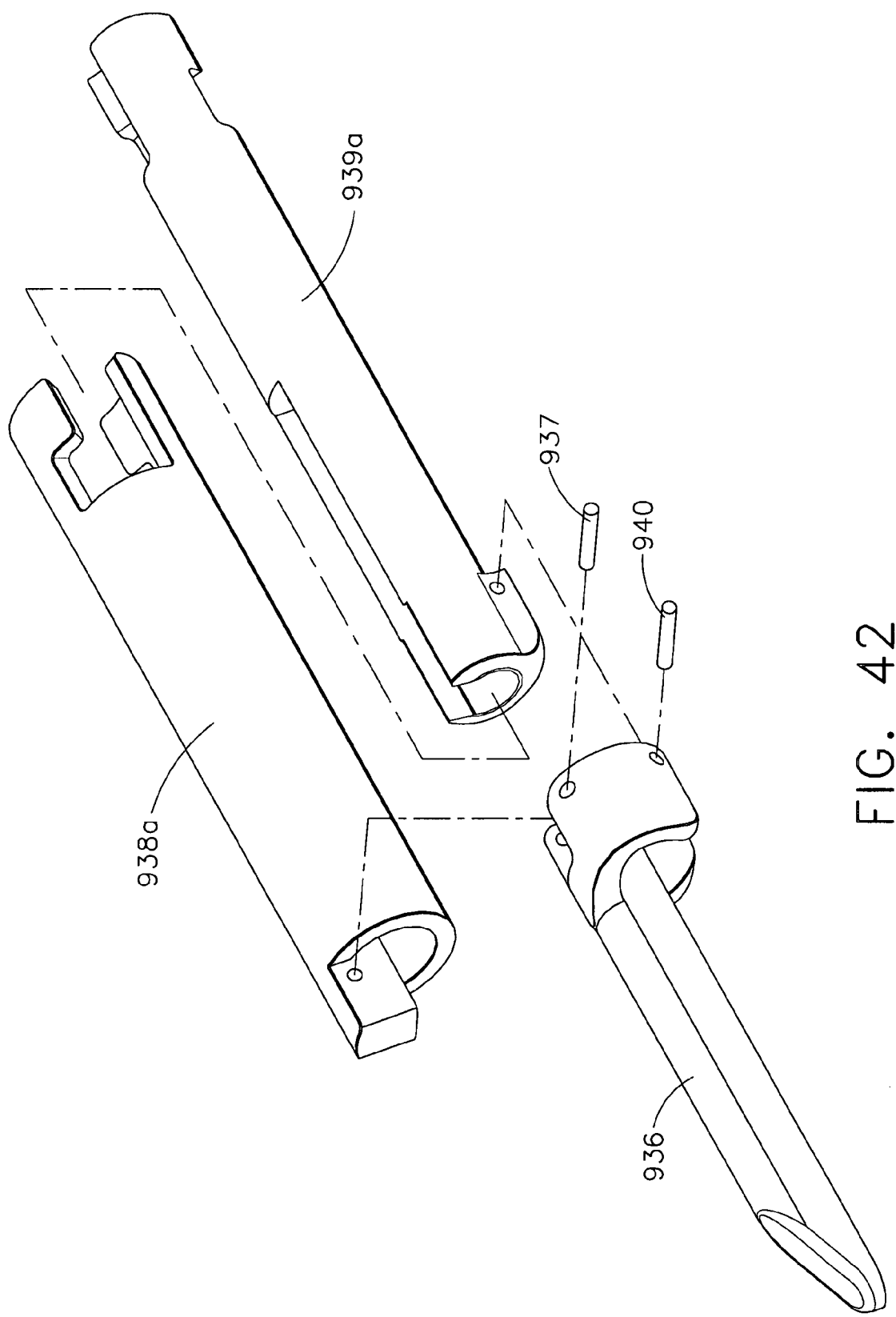
FIG. 42 is an exploded perspective view of the clamp of the surgical instrument of FIG. 34.
Figure 43:
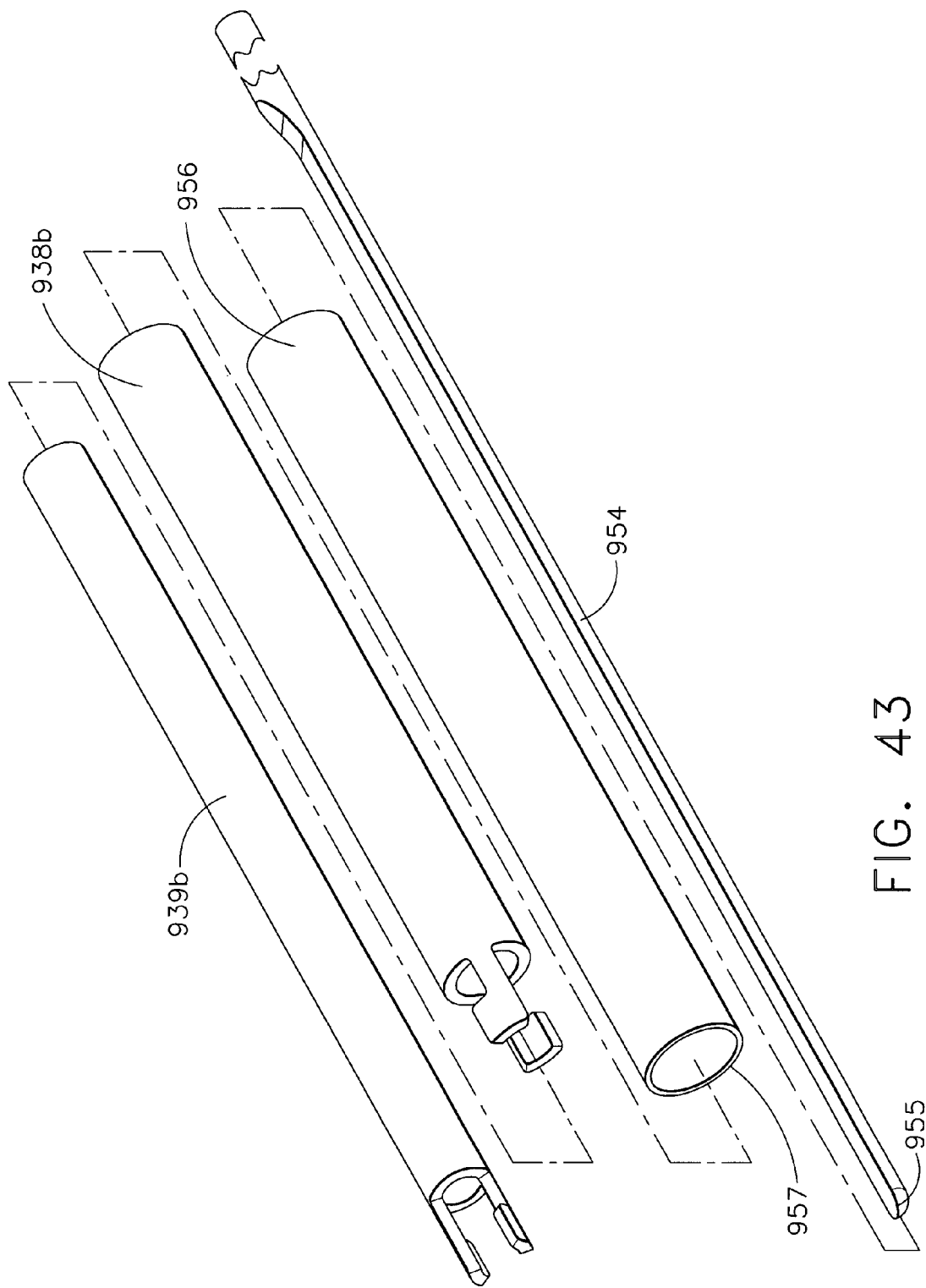
FIG. 43 is an exploded perspective view of the connection between the clamp of FIG. 42 and the actuators of FIGS. 39 and 40.
Figure 44:
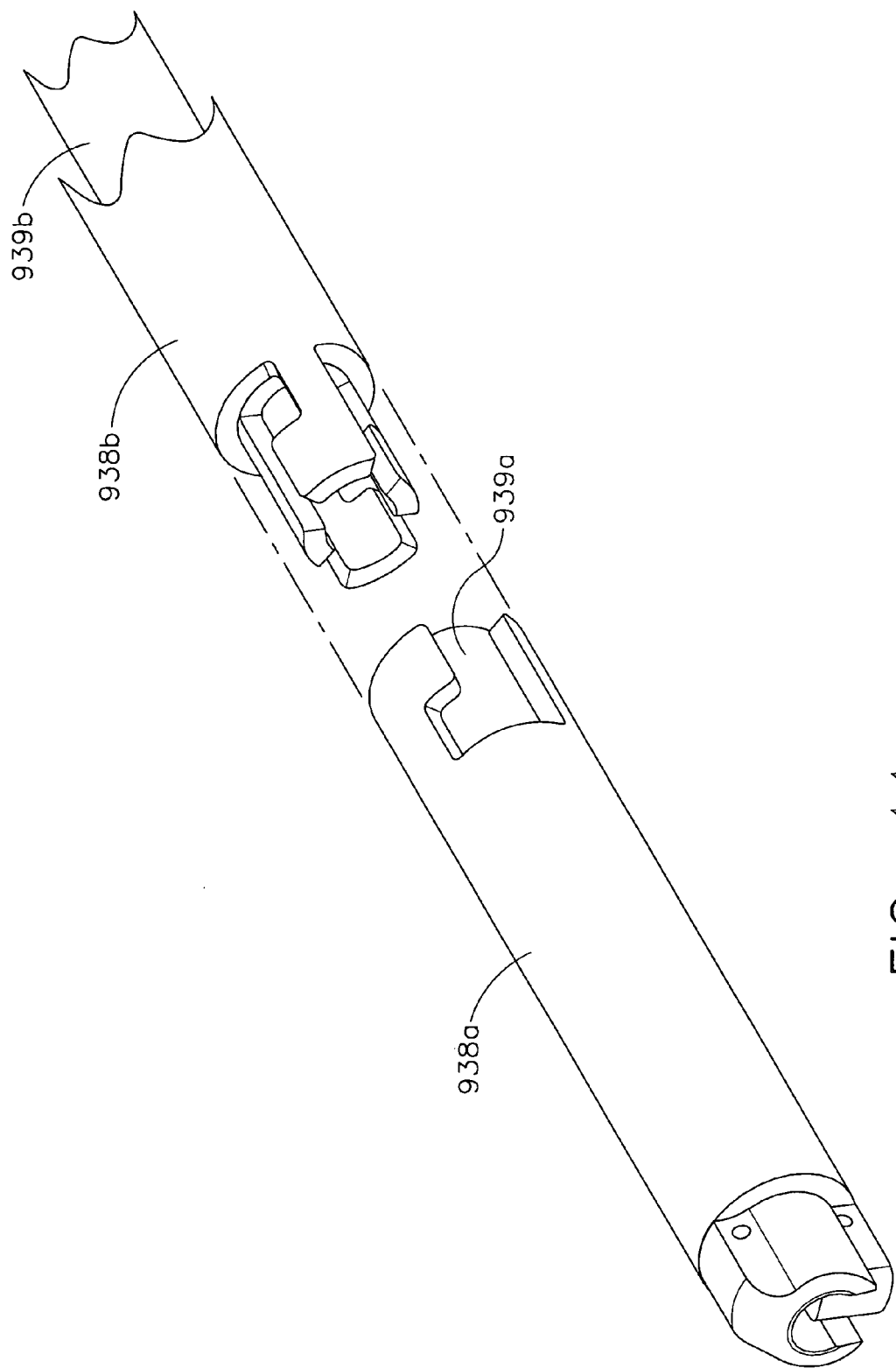
FIG. 44 is an exploded assembly view of portions of the connector of FIG. 43.
Figure 49:
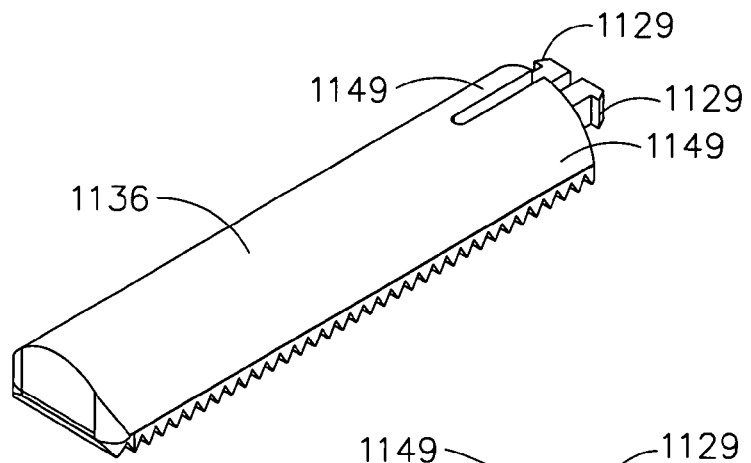
FIG. 49 is a perspective view of the jaw member of FIG. 45.
Figure 50:
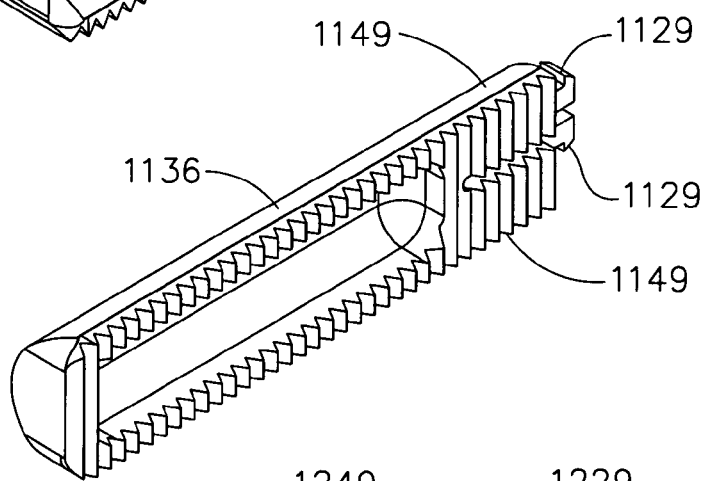
FIG. 50 is a second perspective view of the jaw member of FIG. 45.

In various embodiments, referring to FIGS. 42-44, clamp 935 can be disassembled from surgical instrument 900. More particularly, in at least one embodiment, outer member 938 and inner member 939 can each include two portions which can be disconnected such that clamp 935 can be removed. Referring to FIGS. 42 and 43, outer member 938 can include distal portion 938a and proximal portion 938b which, referring to FIG. 44, can include connector portions to form a bayonet connection therebetween. Similarly, inner member 939 can include distal portion 939a and proximal portion 939b which also include connector portions to form a bayonet connection therebetween. Thus, in order to attach clamp 935 to surgical instrument 900, the respective portions of inner member 939 and outer member 938 are aligned and then rotated to secure them together. Correspondingly, to remove clamp 935, clamp 935 is rotated such that distal portions 938a and 939a become detached from proximal portions 938b and 939b.

In various embodiments, referring to FIGS. 45-50, the retractable clamp of the surgical instrument can include a detachable jaw member. More particularly, surgical instrument 1100 can include retractable clamp 1154 which comprises pivot 1137, jaw connector 1148 and detachable jaw member 1136. Jaw member 1136 can include deflectable legs 1149, for example, which are configured to be received within recess 1127 of jaw connector 1148. In use, deflectable legs 1149 can be squeezed together before they are inserted into recess 1127 and then released to allow legs 1149 to spring outwardly and position feet 1129 behind the walls of recess 1127. In at least one embodiment, feet 1129 can include a beveled surface which can cooperate with the walls of recess 1127 to flex legs 1149 inwardly as they are being inserted therein. Furthermore, in various embodiments, feet 1129 can further include a flat surface, or other contoured surface, which, once feet 1129 are positioned behind the walls for recess 1127, cooperate with recess 1127 to retain detachable jaw member 1136 to jaw connector 1148.

Figure 51:
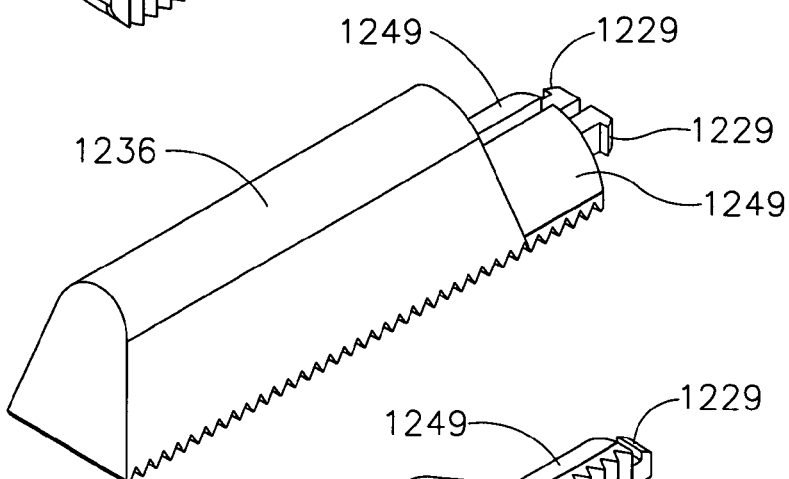
FIG. 51 is a perspective view of a removably attachable jaw member in accordance with an alternative embodiment of the present invention.
Figure 52:
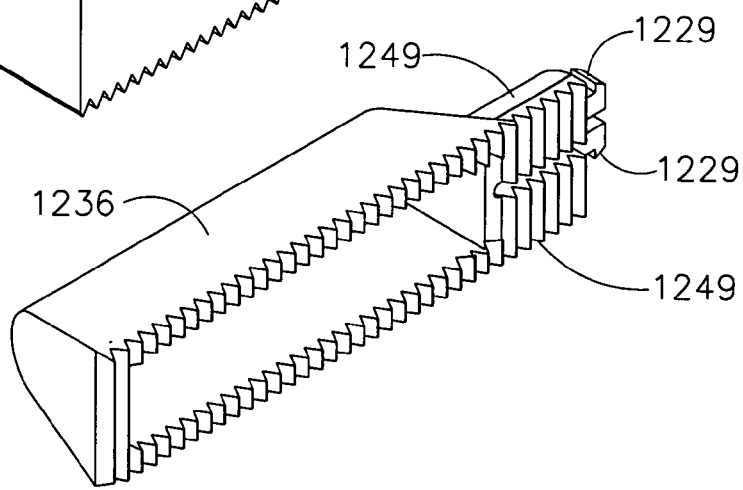
FIG. 52 is a second perspective view of the jaw member of FIG. 51.

In use, a surgeon may be provided with a kit comprising surgical instrument 1100 and a plurality of jaw members. The surgeon may select a desired jaw member from the plurality of jaw members and attach the selected jaw member to surgical instrument 1100 as described above. Thereafter, the surgeon may use the same surgical instrument 1100 with a different jaw member, such as jaw member 1236 illustrated in FIGS. 51 and 52, for example, if desired. To detach jaw member 1136, the surgeon may squeeze legs 1149 together to disengage feet 1129 from recess 1127 such that legs 1149 can pass through recess 1127 and jaw member 1136 can be removed therefrom. Although not illustrated, other attachment means can be used to retain the jaw member to the jaw connector such as a press-fit connection or fasteners, for example.

As described above, a surgical instrument having a retractable clamp can be used for at least three purposes. The first purpose can be to use the clamp to hold tissue or bone against an end-effector where ultrasonic energy applied to the end-effector can be used to cut the tissue or bone therebetween. The second purpose can be to at least partially retract the clamp so that the end-effector can be used to incise or elevate tissue from bone, for example, via ultrasonic energy applied to the end-effector. The third purpose can be to, again, at least partially retract the clamp so that the end-effector can be used without ultrasonic energy applied thereto. In these circumstances, the end-effector can be used to chisel bone, for example, by striking the end of the surgical instrument with a mallet. In various embodiments, an end-effector configured to incise tissue with ultrasonic energy may be unsuitable for striking bone and, as a result, such an end-effector can be replaced with an end-effector more resembling the end of a chisel, for example.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device may be reconditioned for reuse after at least one use. Reconditioning can include a combination of the steps of disassembly of the device, followed by cleaning or replacement of particular elements, and subsequent reassembly. In particular, the device may be disassembled, and any number of particular elements or components of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
   a handle;
   a transducer configured to produce vibrations;
   an end-effector engaged with said transducer, wherein said end-effector defines an axis and a distal tip, and wherein said distal tip is movable relative to said axis by vibrations produced by said transducer;
   an adjustable depth stop movably supported relative to said end-effector, wherein said depth stop includes a distal tip, and wherein said distal tip of said depth stop is movable relative to said distal tip of said end-effector;
   a trigger extending from said handle, wherein said trigger is relatively movable with respect to said handle; and
   a drive mechanism, wherein said depth stop is operably engaged with said drive mechanism, and wherein said trigger is operably engaged with said drive mechanism such that, when said trigger is moved relative to said handle, said distal end of said depth stop is moved relative to said distal end of said end-effector.

2. The surgical instrument of claim 1, wherein said depth stop includes a sheath at least partially surrounding said end-effector.

3. The surgical instrument of claim 1, wherein said vibrations include at least one of vibrations parallel to said axis, vibrations transverse to said axis, and vibrations torsional about said axis.

4. The surgical instrument of claim 1, wherein said depth stop further includes indicia configured to indicate the distance between said distal tip of said end-effector and said distal tip of said depth stop.

5. The surgical instrument of claim 1, wherein said drive mechanism further comprises:
   a ratchet mechanism, wherein said depth stop extends from said ratchet mechanism, and wherein said ratchet mechanism comprises:
      a rack, wherein said depth stop is engaged with said rack;
      a spring engaged with said rack;

a ratchet wheel engaged with said trigger; and a pawl selectively engagable with said ratchet wheel, wherein, when said pawl is engaged with said ratchet wheel, said pawl and said ratchet wheel are configured to move said rack and said distal end of said depth stop with respect to said distal end of said end-effector, and wherein, when said pawl is disengaged from said ratchet wheel, said spring is configured to reposition said rack and said depth stop with respect to said distal end of said end-effector.

6. A method for processing an instrument for surgery, the method comprising:

obtaining the surgical instrument of claim 1;
sterilizing the surgical instrument; and
storing the instrument in a sterile container.

7. A method for processing an instrument for surgery, the method comprising:

obtaining the surgical instrument of claim 1;
detaching said depth stop from the surgical instrument; and
performing one of the following actions:
reforming at least a portion of said depth stop, resterilizing said depth stop, and reattaching said depth stop to the surgical instrument; or
attaching a different said depth stop to the surgical instrument.

8. The surgical instrument of claim 1, wherein said distal tip of said depth stop can be retracted away from said distal tip of said end effector upon an actuation of said trigger.

9. A surgical instrument, comprising:

a handle, comprising:
a housing; and
a trigger movable between an unactuated position and an actuated position;
a transducer, wherein said transducer is configured to produce vibrations;
an end-effector engaged with said transducer, wherein said end-effector defines an axis and a distal tip, and wherein said distal tip is movable relative to said axis by vibrations produced by said transducer; and
a depth stop extending from said housing, wherein said depth stop is operably engaged with said trigger, wherein said depth stop includes a distal tip, and wherein a distance between said distal tip of said depth stop and said distal tip of said end-effector is adjustable by an actuation of said trigger.

10. The surgical instrument of claim 9, wherein said depth stop includes a sheath at least partially surrounding said end-effector.

11. The surgical instrument of claim 9, wherein said vibrations include at least one of vibrations parallel to said axis, vibrations transverse to said axis, and vibrations torsional about said axis.

12. The surgical instrument of claim 9, further comprising:

a ratchet mechanism, wherein said end-effector is connected to said ratchet mechanism, wherein said trigger is operably engaged with said ratchet mechanism such that, when said trigger is moved relative to said handle, said distal end of said end-effector is moved with respect to said distal end of said depth stop.

13. The surgical instrument of claim 9, further comprising:

a ratchet mechanism, comprising:
a rack, wherein said end-effector is engaged with said rack;
a spring engaged with said rack;
a ratchet wheel engaged with said trigger; and
a pawl selectively engagable with said ratchet wheel, wherein, when said pawl is engaged with said ratchet wheel, said pawl and said ratchet wheel are configured to advance said rack and said distal end of said end-effector with respect to said distal end of said depth stop, and wherein, when said pawl is disengaged from said ratchet wheel, said spring is configured to retract said rack and said end-effector with respect to said distal end of said depth stop.

14. The surgical instrument of claim 13, wherein said transducer is engaged with said rack.

15. The surgical instrument of claim 9, wherein said depth stop includes a first portion and a second portion, wherein said second portion is removably connected to said first portion, and wherein said second portion can be disconnected from said first portion to adjust the length of said depth stop.

16. A method for processing an instrument for surgery, the method comprising: obtaining the surgical instrument of claim 9;

sterilizing the surgical instrument; and
storing the instrument in a sterile container.

17. A method for processing an instrument for surgery, the method comprising:

obtaining the surgical instrument of claim 9;
detaching said depth stop from the surgical instrument; and
performing one of the following actions:
reforming at least a portion of said depth stop, resterilizing said depth stop, and reattaching said depth stop to the surgical instrument; or
attaching a different said depth stop to the surgical instrument.

18. The surgical instrument of claim 9, wherein said distal tip of said depth stop can be retracted away from said distal tip of said end effector upon an actuation of said trigger.

19. A surgical instrument kit, comprising:

a surgical instrument, comprising:
a housing;
a transducer configured to produce vibrations; and
an end-effector engaged with said transducer, wherein said end-effector defines an axis and a distal tip, and wherein said distal tip is movable relative to said axis by vibrations produced by said transducer;
a first depth stop, wherein said first depth stop is configured to extend from said housing, wherein said first depth stop includes a distal tip, and wherein, when said first depth stop is assembled to said housing, said distal tip of said end-effector and said distal tip of said first depth stop define a first distance therebetween; and
a second depth stop, wherein said second depth stop is configured to extend from said housing, wherein said second depth stop includes a distal tip, wherein, when said second depth stop is assembled to said housing, said distal tip of said end-effector and said distal tip of said second depth stop define a second distance therebetween, and wherein said first distance is different than said second distance.

20. The surgical kit of claim 19, wherein said housing includes one of a projection and a slot, wherein said first depth and said second depth stop each include the other of said projection and said slot, and wherein said slot is configured to receive said projection and attach said depth stops to said housing.

21. The surgical kit of claim 20, wherein, when said projection is positioned in said slot, said projection and said slot are in a press-fit engagement.

22. A surgical instrument, comprising:

a handle, comprising:
a housing;
a trigger rotatably mounted to said housing; and
a transducer configured to produce vibrations;

an end-effector operably engaged with said transducer, wherein said end-effector comprises an axis and a distal tip, and wherein said distal tip is movable relative to said axis by vibrations produced by said transducer;

an adjustable depth stop comprising a distal tip; and a drive mechanism operably engaged with said trigger and said depth stop wherein, when said trigger is moved relative to said handle, said distal end of said depth stop is moved relative to said distal end of said end-effector, and wherein said distal end of said depth stop can be moved concurrently with the production of vibrations from said transducer.

23. The surgical instrument of claim 22, wherein said distal end of said depth stop can be retracted away from said distal end of said end effector upon an actuation of said trigger.

* * * * *